United States Patent
Zhang et al.

(10) Patent No.: US 10,919,856 B2
(45) Date of Patent: Feb. 16, 2021

(54) CYCLOHEXENE COMPOUNDS AND USE THEREOF

(71) Applicant: GUANGZHOU HENOVCOM BIOSCIENCE CO. LTD, Guangzhou (CN)

(72) Inventors: Jiancun Zhang, Guangzhou (CN); Kun Wang, Guangzhou (CN); Yan Liu, Guangzhou (CN); Deyao Li, Guangzhou (CN)

(73) Assignee: GUANGZHOU HENOVCOM BIOSCIENCE CO. LTD., Guangzhou (CN)

( * ) Notice: Subject to any disclaimer, the term of this patent is extended or adjusted under 35 U.S.C. 154(b) by 0 days.

(21) Appl. No.: 16/331,797

(22) PCT Filed: Sep. 5, 2017

(86) PCT No.: PCT/CN2017/100582
§ 371 (c)(1),
(2) Date: Apr. 25, 2019

(87) PCT Pub. No.: WO2018/045950
PCT Pub. Date: Mar. 15, 2018

(65) Prior Publication Data
US 2019/0241520 A1     Aug. 8, 2019

(30) Foreign Application Priority Data

Sep. 9, 2016 (CN) .......................... 2016 1 0814412

(51) Int. Cl.
| C07D 211/42 | (2006.01) |
| A61K 31/451 | (2006.01) |
| A61P 31/16 | (2006.01) |
| C07D 211/22 | (2006.01) |
| A61P 11/00 | (2006.01) |
| C07D 211/32 | (2006.01) |

(52) U.S. Cl.
CPC .......... *C07D 211/42* (2013.01); *A61K 31/451* (2013.01); *A61P 11/00* (2018.01); *A61P 31/16* (2018.01); *C07D 211/22* (2013.01); *C07D 211/32* (2013.01)

(58) Field of Classification Search
CPC .................................................... C07D 211/42
See application file for complete search history.

(56) References Cited

FOREIGN PATENT DOCUMENTS

| CN | 103224464 A | 7/2013 |
| CN | 106496100 A | 3/2017 |

OTHER PUBLICATIONS

International Search Report for PCT/CN2017/100582.
Written Opinion for PCT/CN2017/100582.
International Search Report for PCT/CN2017/100582M, dated Oct. 25, 2017.
Written Opinion for PCT/CN2017/100582, dated Oct. 25, 2017.

*Primary Examiner* — Brian E McDowell
(74) *Attorney, Agent, or Firm* — Schmeiser, Olsen & Watts, LLP

(57) ABSTRACT

A cyclohexene compound and use thereof, which relates to the technical field of pharmaceutical chemistry is provided. The cyclohexene compound is the cyclohexene compound having a structural formula I or a pharmaceutically acceptable salt, an ester group prodrug or a stereoisomer thereof. It is verified by activity assay for influenza NA that the cyclohexene compound has a great inhibiting activity against both wild-typed and drug-resistant influenza viruses, and the inhibiting activity $IC_{50}$ of some compounds against wild-typed and drug-resistant influenza viruses is lower than 5 nM, showing significant inhibiting effect on influenza viruses. This shows that the cyclohexene compound or a pharmaceutically acceptable salt or a stereoisomer thereof has superior application prospect on preparing anti-influenza drugs, thereby providing a new drug choice for treating influenza clinically.

6 Claims, No Drawings

CYCLOHEXENE COMPOUNDS AND USE THEREOF

CROSS-REFERENCE TO RELATED APPLICATIONS

This application claims priority to PCT Application No. PCT/CN2017/100582, having a filing date of Sep. 5, 2017 based off Chinese application No. 201610814412.8 having a filing date of Sep. 9, 2016, the entire contents of both of which are hereby incorporated by reference.

FIELD OF TECHNOLOGY

The following relates to the technical field of pharmaceutical chemistry, particularly, it relates to a cyclohexene compound and use thereof.

BACKGROUND

Influenza is one of common respiratory diseases, and it causes patients to be weak, have a variety of complications, be hospitalized and even die in severe cases. In addition, influenza is highly infectious, and is easily spread between the elder and the people with weak resistibility, even resulting in influenza pandemic. According to World Health Organization, during seasonal flu outbreak, approximately 5%-15% people are affected by respiratory infection, and there are up to 600 million-1.2 billion cases of influenza every year, wherein about 0.3million-0.5million people die of infection of the influenza viruses.

There are three types of human influenza viruses, that is, influenza virus A, B, and C. Influenza virus A is the most harmful, and has caused worldwide pandemics several times. Influenza virus B and C has lower pathogenicity on human. There are also various subtypes for each type of influenza viruses, and hemagglutinin (HA, or H) and neuraminidase (NA, or N) on their surface are important classification indicators. For the influenza virus A, there are 15 types of H, and 9 types of N. Although there are various combination ways of H and N, H1N1, H2N2 and H3N2 are the main influenza virus which can spread among humans and lead to respiratory diseases. Almost all the combinations of 15 H and 9 N have been found in avian species, and it is found that some subtypes of avian influenza virus from avian, specifically H5N1, H5N2, H7N1, H9N2 and currently pandemic H7N9, can infect humans, and cause to so-called avian influenza.

Influenza virus A has a wide range of hosts and segmenting genome, and during its infection and replication, gene mutation or gene recombination easily occurs so that a new mutant may be created, which is a basic reason why influenza virus antigen has high variability, therefore stable and durable immunity against the influenza virus antigen is difficultly generated by a human.

With regarding the currently used influenza vaccine, its prevention efficiency against influenza-like illness only reaches 60%-70%, and its protection efficiency for the elder or the people with underlying disease is only 40%. The spread of influenza virus is closely associated with HA and NA. HA can attach the virus to host cells. After the influenza virus HA is bonded to neuraminic acid residues on the surface of the host cells, virus invades into the cells and replicate within the cells to produce a new progeny virus, which will release from the surface of the host cells in a budding form. As influenza virus has the capacity of envelope synthesis by utilizing the host cell membrane, the neuraminic acid residues also exist on the surface of newly synthesized progeny virus. NA can release the new virus out from the host cells through the action of neuraminidase in recipient cell. In current clinical applications, there are mainly two types of drugs effective against influenza virus, M2 ion channel blocker and NA inhibitor.

M2 ion channel blocker is a conventional drug for treating influenza virus A, and there are two types, that is, Amantadine (molecular formula: $C_{10}H_{17}N \cdot HCl$) and Rimantadine (molecular formula: $C_{12}H_{21}N \cdot HCl$). Currently, only Amantadine is clinically used in China. These two types of drugs inhibit the processes of virus entering sensitive cells and nucleic acids release through changing surface charge of the host cells, so that the replication of the virus is inhibited. However, after the drug was administrated for several hours, the symptoms such as insomnia, distraction and nervousness, etc. will appear due to side effects of these drugs. In addition, the spread of drug-resistant virus strains is liable to appear in the application of such types of drugs, and if the above two drugs are used for the treatment of influenza, about ⅓ patients will develop drug-resistant virus strains presenting cross-resistance. Generally, drug-resistant phenomenon occurs after treatment for 2-3 days, and the drug is only effective to influenza virus A, therefore its use in clinical application is restricted. M2 ion channel blocker is more likely to cause the emergence and spread of drug-resistant virus strains, compared to NA inhibitor, because point mutation occurs on a single amino acid located on locus of M protein of the virus, modifying the amino acid on transmembrane domain of virus M2 protein, and drug-resistant mutant strains are existed as being in subgroups.

NA inhibitor selectively inhibits the activity of NA and prevents the progeny virus from replicating and releasing from the host cells, thereby effectively preventing the influenza and reliving symptoms. Oseltamivir phosphate is an NA inhibitor developed by American Gilead Sciences company, and in 10 Oct., 1999, it first appeared on the market in Switzerland, with a chemical name of ethyl (3R,4R,5S)-4-acetamido-5-amino-3-(1-ethylpropoxyl)-1-cyclohexene-1-carboxylate phosphate and a brand name of Tamiflu, which is a ethyl ester-type prodrug formed by introduction of hydrophobic group via acetylation based on the structure of new carbon ring NA inhibitor GS4071 for influenza virus. Its affinity with NA of influenza virus is about 1 million times larger than that with the same types of human enzymes, and it almost has no inhibiting effect on other viruses, bacterium or human NA, thus so far Oseltamivir phosphate is considered as an anti-influenza drug with the highest specificity, and also won't inhibit body's immune response against influenza virus. Once Oseltamivir is absorbed via gastrointestinal tract, it is immediately metabolized to Oseltamivir carboxylate. In the oral preparation, at least 75% ingredient participates in system circulation in a form of Oseltamivir carboxylate. It has been proved by clinical assays that severity level of influenza symptoms may be reduced by 40% after the Oseltamivir being taken twice a day for five days, 75 mg at a time. The early taking of Oseltamivir maximizes its pharmaceutical efficacy, and the state of an illness will be shortened by 3.1 days in a case that Oseltamivir was administrated within 12 hours after the onset of the symptoms, compared to that the drug is administrated after 48 hours since the onset of the symptoms. Oseltamivir can quickly relieve the hyperpyrexia caused by influenza, and it has obvious efficacy and great drug compliance. Oseltamivir phosphate not only has a perfect effect on treatment of avian influenza, but also achieves a significant effect on the treatment of H7N9 avian influenza patients, if the administration is performed within 3 hours after the infection. Thus, so far Tamiflu is the first choice in anti-influenza drugs.

However, the influenza virus developed drug-resistance against the anti-influenza drug in view that it is liable to mutate. It has been found that the pandemic influenza virus (H1N1 pdm 09) in 2009 showed the drug-resistance to Oseltamivir phosphate.

SUMMARY

An aspect relates to a cyclohexene compound, which has good inhibiting activity against influenza viruses, specifically against those virus strains which are drug-resistant to Oseltamivir phosphate.

In order to achieve the above aspect, the present disclosure provides a cyclohexene compound having a structural formula I or a pharmaceutically acceptable salt, an ester prodrug or a stereoisomer thereof:

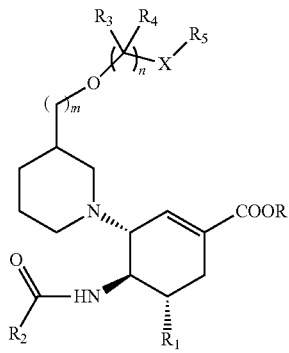

I wherein,

R is selected from H, an ion of M, or $C_1$~$C_6$ alkyl;

M is selected from $Na^+$, $Ca^{2+}$, $Mg^{2+}$, $K^+$, $Li^+$, or $(HNR_6R_7R_8)^+$;

$R_6$, $R_7$ and $R_8$ are independently selected from H, $C_1$~$C_4$ alkyl, substituted $C_1$~$C_4$ alkyl, $C_3$~$C_6$ cycloalkyl, substituted $C_3$~$C_6$ cycloalkyl, $C_3$~$C_6$ heterocyclyl, or substituted $C_3$~$C_6$ heterocyclyl;

$R_1$ is selected from amino, amidino, or guanidyl;

$R_2$ is selected from H, $C_1$~$C_4$ alkyl, or $C_1$~$C_4$ alkenyl;

m is selected from 0, or 1;

$R_3$ and $R_4$ are independently selected from: H, $C_1$~$C_4$ alkyl, substituted $C_1$~$C_4$ alkyl, $C_3$~$C_6$ cycloalkyl, substituted $C_3$~$C_6$ cycloalkyl, $C_3$~$C_6$ heterocyclyl, or substituted $C_3$~$C_6$ heterocyclyl;

n is selected from 1, 2, 3, or 4;

X is absent, or X is selected from $CH_2$, O, S, NHCOO, OCONR$_9$R$_{10}$, or NHSO$_2$;

$R_5$ is absent, or $R_5$ is selected from H, $C_1$~$C_4$ alkyl, substituted $C_1$~$C_4$ alkyl, $C_3$~$C_6$ cycloalkyl, substituted $C_3$~$C_6$ cycloalkyl, $C_3$~$C_6$ heterocyclyl, or substituted $C_3$~$C_6$ heterocyclyl; and $R_9$ and $R_{10}$ are independently selected from H, $C_1$~$C_4$ alkyl, substituted $C_1$~$C_4$ alkyl, $C_3$~$C_6$ cycloalkyl, or substituted $C_3$~$C_6$ cycloalkyl, or $R_9$ and $R_{10}$ together with the atom to which they are attached form a $C_3$~$C_6$ heterocyclic ring containing O, S, NH.

In some examples, a compound having a structural formula II is provided as follows:

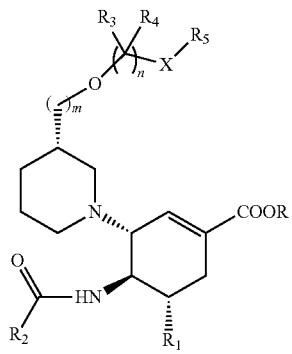

II wherein, R, $R_1$, $R_2$, $R_3$, $R_4$, $R_5$, X, m and n are defined as hereinbefore.

In some examples, a compound having a structural formula III is provided as follows:

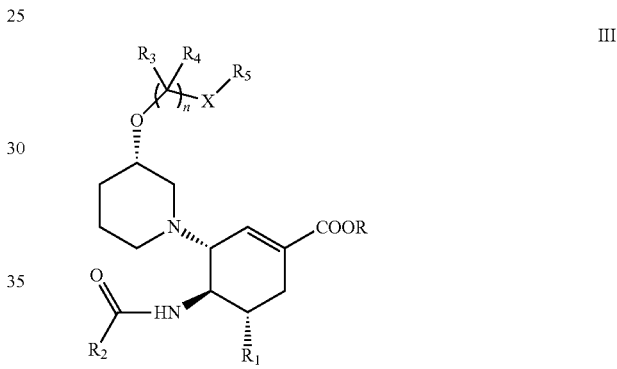

III wherein,

X is absent, or X is selected from $CH_2$, O, S, NHCOO, or OCONR$_9$R$_{10}$, or NHSO$_2$; and R, $R_1$, $R_2$, $R_3$, $R_4$, $R_5$, $R_9$, $R_{10}$ and n are defined as hereinbefore.

In some examples, R is selected from H;

$R_1$ is selected from amino, or guanidyl;

$R_2$ is selected from $C_1$~$C_4$ alkyl;

$R_3$ and $R_4$ are independently selected from H;

n is selected from 2;

X is selected from O, NHCOO, NHCOO, or OCONR$_9$R$_{10}$;

$R_5$ is absent, or $R_5$ is selected from H, $C_1$~$C_4$ alkyl, substituted $C_1$~$C_4$ alkyl, $C_3$~$C_6$ cycloalkyl, substituted $C_3$~$C_6$ cycloalkyl, $C_3$~$C_6$ heterocyclyl, or substituted $C_3$~$C_6$ heterocyclyl; and $R_9$ and $R_{10}$ are independently selected from H, $C_1$~$C_4$ alkyl, substituted $C_1$~$C_4$ alkyl, $C_3$~C6 cycloalkyl, or substituted $C_3$~$C_6$ cycloalkyl, or $R_9$ and $R_{10}$ together with the atom to which they are attached form a $C_3$~$C_6$ heterocyclic ring containing O, S, NH.

In some examples, a compound having a structural formula IV is provided as follows:

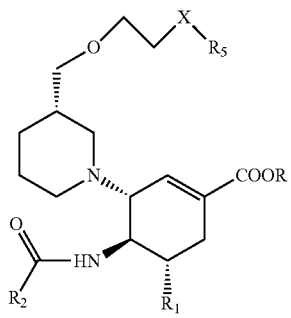

IV wherein, X is selected from CH$_2$, or O:

R$_5$ is selected from H, C$_1$~C$_4$ alkyl, C$_3$~C$_6$ cycloalkyl, substituted C$_3$~C$_6$ cycloalkyl, C$_3$~C$_6$ heterocyclyl, or substituted C$_3$~C$_6$ heterocyclic group; and R, R$_1$ and R$_2$ are defined as hereinbefore.

In some examples, substituted C$_1$~C$_4$ alkyl is selected from: hydroxyethyl, methoxyethyl, ethoxyethyl; substituted C$_3$~C$_6$ cycloalkyl is selected from: cyclopropyl substituted methyl; and C$_3$~C$_6$ cycloalkyl is selected from: 4-carbonyloxymorpholinyl.

It is a further aspect of the present disclosure to disclose a use of the cyclohexene compound or a pharmaceutically acceptable salt, an ester prodrug or a stereoisomer thereof in preparation of drugs for preventing and treating influenza viruses.

It is a further aspect of the present disclosure to disclose a pharmaceutical composition, comprising the foresaid cyclohexene compound or a pharmaceutically acceptable salt, an ester prodrug or a stereoisomer thereof, and a pharmaceutically acceptable excipient or carrier.

In contrast to the known art, the present disclosure has the following advantages:

It has been proved by the influenza viruses NA activity assay that the cyclohexene compound or a pharmaceutically acceptable salt or a stereoisomer thereof of the present disclosure has a great inhibiting activity against wild-typed and drug-resistant influenza viruses, and the inhibiting activity IC$_{50}$ of some compounds against wild-typed and drug-resistant influenza viruses (specifically against drug-resistant H274Y mutant) is smaller than 5 nM, showing significant inhibiting effect on influenza viruses. This shows that the cyclohexene compound or a pharmaceutically acceptable salt or stereoisomer thereof has superior application prospect on preparing anti-influenza drugs, and provides a new drug choice for treating influenza clinically.

DETAILED DESCRIPTION

The term "alkyl" herein refers to saturated hydrocarbyl or unsaturated chained alkyl, "chained alkyl" refers to linear or branched alkyl. For example, C$_1$~C$_4$ alkyl refers to saturated or unsaturated, linear or branched alkyl having 1~4 carbon atoms, wherein examples of saturated linear alkyl comprise but are not limited to ethyl, n-propyl and so on; examples of saturated branched alkyl comprise but are not limited to isopropyl group, tertiary butyl and so on; examples of unsaturated linear alkyl comprise but are not limited to ethenyl, propenyl and so on, and examples of unsaturated branched alkyl comprise but are not limited to 2-methylpropenyl and so on; "cycloalkyl" refers to alkyl having cyclic structure, for example, C$_3$~C$_6$ cycloalkyl refers to saturated or unsaturated cyclic alkyl having 3~6 carbon atoms, wherein examples of saturated cycloalkyl comprise but are not limited to cyclopropyl, cyclobutyl, cyclopropyl substituted with methyl, and examples of unsaturated cycloalkyl comprise but are not limited to cyclopentene and so on. The term "heterocyclic group" refers to a group which is monocyclic, bicyclic or tricyclic, wherein one or more carbon atoms on the ring are independently and optionally substituted by heteroatoms selected from N, O, P, S and so on, such as, pyrrolidyl, tetrahydrofuryl, dihydrofuryl, tetrahydrothienyl, tetrahydropyranyl, dihydropyranyl, tetrahydrothiapyranyl, piperidyl, morpholinyl, thiomorpholinyl, thioxane group, thiazolidine group, oxazolidine group,or piperazinyl.

The term "substituted" means that hydrogen group in a specific structure is replaced by a specified substituent.

The present disclosure comprises the compound of formula I-IV in a free form and also comprises a pharmaceutically acceptable salt and stereoisomer thereof. The pharmaceutically acceptable salt of the present disclosure can be synthesized from the compounds comprising alkaline or acidic parts of the present disclosure through common chemical methods. In general, the salt of alkaline compound is synthesized through ion exchange chromatography or through a reaction between free alkaline and inorganic or organic acid in a form of desirable salt, which are in chemical calculated amount or excess amount in suitable solvents or combinations thereof. Similarly, the salt of acidic compound is prepared through a reaction with a suitable inorganic or organic alkaline.

Therefore, the pharmacologically acceptable salt of the present disclosure includes conventional non-toxic salt of the present disclosure synthesized by the reaction between the alkaline compounds of the present disclosure and inorganic or organic acids. For example, the conventional non-toxic salt includes the salt prepared from inorganic acids, such as hydrochloric acid, hydrobromic acid, sulfuric acid, sulfamic acid, phosphoric acid, or nitric acid, and also includes the salt prepared from organic acids, such as acetic acid, propionic acid, succinic acid, glycolic acid, lactic acid, malic acid, tartaric acid, citric acid, ascorbic acid, maleic acid, hydroxy maleic acid, benzene acetic acid, glutamic acid, benzoic acid, salicylic acid, fumaric acid, toluenesulfonic acid, methanesulfonic acid, ethanedisulfonic acid, oxalic acid, hydroxyethanesulphonic acid, or trifluoroacetic acid.

If the compound of the present disclosure is acidic, the appropriate "pharmaceutically acceptable salt" means a salt prepared from a pharmaceutically acceptable non-toxic alkaline comprising inorganic or organic alkaline. The salt prepared from inorganic alkaline includes ammonium salt, calcium salt, lithium salt, magnesium salt, potassium salt, sodium salt, zinc salt, etc., and ammonium salt, calcium salt, magnesium salt, potassium salt and sodium salt. The salt prepared from organic non-toxic alkaline includes primary amine, secondary amine, tertiary amine, (quaternary ammonium) salt, and substituted amines comprising natural substituted amines, cyclic amines and alkaline ion exchange resin such as arginine, choline, diethylamine, 2-diethylaminoethanol, 2-dimethylaminoethanol, ethanolamine, ethylenediamine, N-ethylmorpholine, N-ethyl piperidine, glucosamine, histidine, isopropylamine, lysine, methylglucosamine, morpholine, piperazine, piperidine polyamine resin, triethylamine, trimethylamine, tripropylamine, or tromethamine.

In addition to the conventional methods disclosed in the literatures or exemplified in the experimental procedures, the compound of the present disclosure can be prepared by the method described in the following synthetic approaches.

The compound and synthetic method described in the present disclosure can be better understood in combination with the following synthesis schemes. The synthesis schemes describe methods for preparing compounds of the present disclosure, and the methods are merely illustrative descriptions for purpose of explanation without limitation of the scope of the disclosure.

The method for preparing a starting material ethyl (3R, 4R, 5S)-4-acetamido-5-azido-3-acetoxy-1-cyclohexene-1-carboxylate in the following examples is seen from J. Am. Chem. Soc., 1997(119): 681-690.

EXAMPLE 1 a) Preparation of ethyl (3R,4S,5S)-4-acetamido-5-azido-3-((3S)-3-(2-methoxylethoxyl)piperidin)-1-cyclohexene-1-carboxylate.

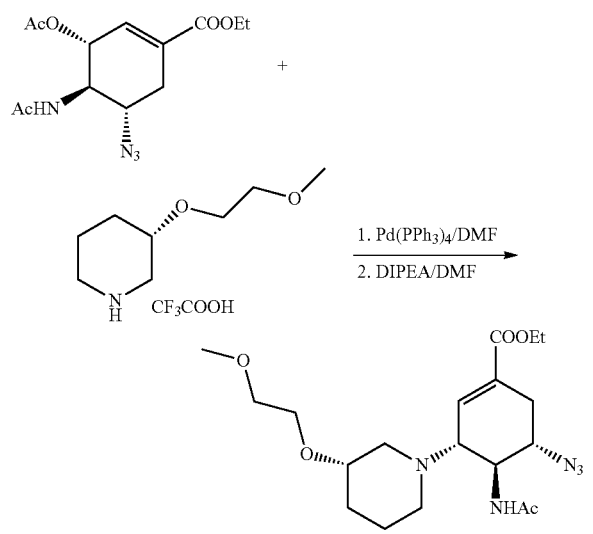

According to the above equation, 20 mmol of ethyl (3R,4R,5S)-4-acetamido-5-azido-3-acetoxyl-1-cyclohexene-1-carboxylate and 1 mmol of tetrakis (triphenylphosphine) palladium were added into a dry twin-neck flask, and after the air in the system was replaced with nitrogen gas twice, 40 mL of redistilled DMF (dimethylformamide) was added with an injector and well stirred. 40 mmol of DIPEA (N,N-Diisopropylethylamine) was then added and stirred, after it is cooled to 0° C., the solution (40 mL) of (3S)-3-(2-methoxylethoxyl)piperidin trifluoroacetate in DMF was slowly dripped into. The mixture was stirred at 0° C. for 20 minutes after the dripping, then it was placed in an oil bath to react at 70° C. for 1 hour. Gradually cooled it to 0° C. once the TLC (DCM:MeOH=10:1) indicated the reaction was completed. Water in the same volume was slowly dripped into, and after the mixture was stirred well, it was extracted with EA (ethyl acetate) and evaporated to dryness. DMF is removed by using an oil pump, and a brown viscous object was obtained. After an elution through column purification (MeOH: DCM=1:50), 3.8 g yellow-white powder solid was obtained, with a yield of 46.4%.

The characterization analysis of the product:
$^1$H—NMR(400 MHz, CDCl$_3$):δppm6.880(s,1H,NH),5.736-5.717(dd,1H,2-CH),4.221-4.187(q,2H,CH$_2$CH$_3$),3.895-3.868(dd,1H,4-CH),3.855-3.780(dd,1H,3-CH),3.754-3.487(t,4H, OCH$_2$CH$_2$O),3.381(s,3H$_2$OCH$_3$),2.907-2.851(m,1H,NCH$_2$CHOCH$_2$),2.815-2.790(d,1H,NCH$_2$CHOCH$_2$),2.731-2.705(t,1H,NCH$_2$CH$_2$),2.519-2.496(t,1H,NCH$_2$CH$_2$),2.293-2.271(d,1H,NCH$_2$CHOCH$_2$),2.244-2.207(dd,1H,5-CH),2.037-1.956(dd,1H,6-CH$_2$),1.933(s,3H,COCH$_3$),1.797-1.714(dd,1H,6-CH$_2$),1.704-1.685(m,1H,NCH$_2$CH$_2$CH$_2$),1.393-1.368(m,2H,NCH$_2$CH$_2$CH$_2$),1.315-1.300(m,1H,NCH$_2$CH$_2$CH$_2$),1.298-1.280(t,3H,CH$_2$CH$_3$).
ESI-MS m/z: 410.3(M+H)$^+$.

b) Preparation of ethyl (3R,4R,5S)-4-acetamido-5-amino-3-((3S)-3-(2-methoxylethoxyl)piperidin)-1-cyclohexene-1-carboxylate.

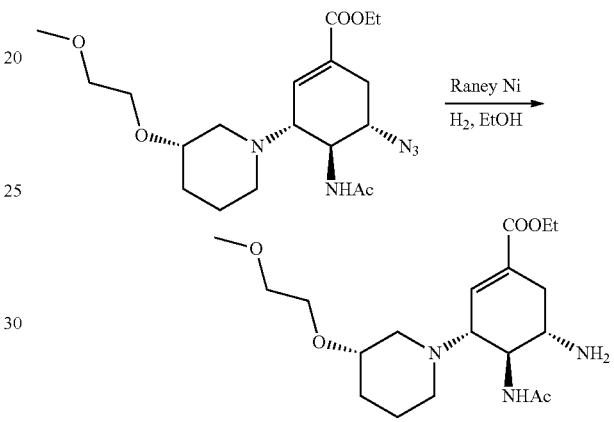

According to the above equation, ethyl (3R,4S,5S)-4-acetamido-5-azido-3-((3S)-3-(2-methoxylethoxyl)piperidin) -1-cyclohexene-1-carboxylate was added into a single-neck flask, and Raney Ni in catalytic amount and 40 mL of absolute ethyl alcohol were then added and well stirred. The air in the system was replaced with hydrogen gas, the mixture was continually stirred at room temperature for 2 hours. After the TLC (DCM:MeOH=10:1) indicated the reaction was completed, Raney Ni was filtered out with diatomite. The solvent was then evaporated, purified by column (DCM:MeOH=5:1), and a white foam solid was obtained.

The characterization analysis of the product:
$^1$H-NMR(400 MHz,CDCl$_3$):δppm6.883(s,1H,NH),5.574-5.513(dd,1H,2-CH), 4.197-4.171(q,2H,CH$_2$CH$_3$),3.839-3.816(dd,1H,4-CH),3.793-3.790(dd,1H,3-CH),3.644-3.591(t,4H,OCH$_2$CH$_2$O),3.555-3.508(dd,1H,5-CH),3.369(s,3H, OCH$_3$),3.251-3.227(m,1H,NCH$_2$CHOCH2),2.896-2.890(d,1H,NCH$_2$CHOCH$_2$),2.884-2.871(t,1H,NCH$_2$CH$_2$),2.858-2.850(t,1H,NCH$_2$CH$_2$),2.837-2.796(d,1H,NCH$_2$CHOCH$_2$),2.700-2.673(dd,1H,6-CH$_2$),2.515-2.468(dd,1H,6-CH$_2$),2.174-2.123(m,3H,NCH$_2$CH$_2$CH$_2$, NCH$_2$CH$_2$CH$_2$), 1.988(s,3H,COCH$_3$), 1.792-1.690(m,1H,NCH$_2$CH$_2$CH$_2$), 1.314-1.295(t,3H,CH$_2$CH$_3$).
ESI-MS m/z: 384.2(M+H)$^+$.

c) Preparation of ethyl (3R,4R,5S)-4-acetamido-5-((tert-butyloxycarbonyl) amino)-3-((3S)-3-(2-methoxylethoxyl) piperidin)-1-cyclohexene-1-carboxylate.

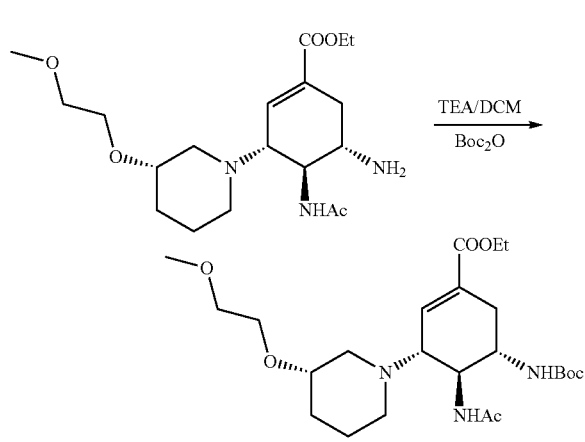

According to the above equation, 0.5 mmol of ethyl (3R,4R,5S)-4-acetamido-5-amino-3-((3S)-3-(2-methoxylethoxyl)piperidin)-1-cyclohexene-1-carboxylate was added into a single-neck flask, and 2 mL of DCM and 0.75 mmol of TEA were then added and stirred at room temperature till completely dissolved. 0.75 mmol of Boc$_2$O was dripped into and stirred at room temperature for 30 minutes. After the TLC (DCM:MeOH=20:1) indicated the reaction was completed, small amount of water was added for extraction with DCM, and anhydrous sodium sulfate was used for drying before the solvent being evaporated to dryness. After being purified by column (DCM:MeOH=20:1), a white solid was obtained. ESI-MS m/z for the product: 484.2(M+H)$^+$.

d) Preparation of (3R,4R,5S)-4-acetamido-5-((tert-butyloxycarbonyl) amino)-3-((3S)-3-(2-methoxy ethoxyl)piperidin)-1-cyclohexene-1-carboxylic acid.

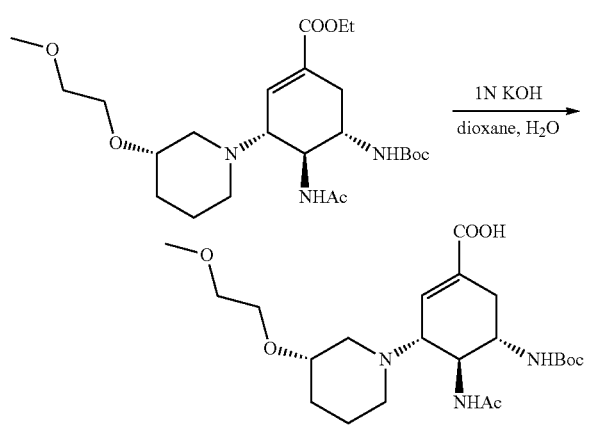

According to the above equation, 160 mg of ethyl (3R,4R,5S)-4-acetamido-5-((tert-butyloxycarbonyl) amino)-3-((3S)-3-(2-methoxylethoxyl)piperidin)-1-cyclohexene-1-carboxylate was added into a single-neck flask, and 5.5 ml of 1,4-dioxane, 0.5 ml of water and 0.5 ml of 1N KOH aqueous solution were then added and stirred overnight at room temperature. After the TLC (DCM:MeOH=20:1) indicated that the reaction was completed, the solvent was evaporated to dryness, and dried by using an oil pump. Methanol was used for dissolving, and pH was regulated to 5 with acid resin. After being filtered, evaporated to dryness, and purified by the column (DCM:MeOH=5:1), a white solid was obtained.

The characterization analysis of the product:

$^1$H-NMR(400 MHz,MeOD):δppm6.777(dd,1H,2-C$\underline{H}$),4.058-4.007(dd,1H,4-C$\underline{H}$), 3.684-3.671(dd,1H,5-C$\underline{H}$),3.660-6.652(dd,1H,3-C$\underline{H}$),3.628-3.620(t,4H$_2$OC$\underline{H}_2$C$\underline{H}_2$O),3.360(s,3H,OC$\underline{H}_3$),2.976-2.951(m,1H,NCH$_2$C$\underline{H}$OCH$_2$),2.926-2.902(d,1H,NC$\underline{H}_2$CHOCH$_2$),2.763-2.708(t,1H,NC$\underline{H}_2$CH$_2$),2.622-2.610(t,1H,NC$\underline{H}_2$CH$_2$),4.452-2.490(d,1H,NC$\underline{H}_2$CHOCH$_2$),2.246-2.176(dd,1H,6-C$\underline{H}_2$),1.970(s,3H,COC$\underline{H}_3$),1.950-1.900(dd, 1H,6-C$\underline{H}_2$),1.790-1.775(m,1H,NCH$_2$CH$_2$C$\underline{H}_2$),1.595-1.525(m,1H,NCH$_2$C$\underline{H}_2$CH$_2$), 1.442(s,9H,O(C$\underline{H}_3$)$_3$),1.361-1.292(m,2H, NCH$_2$CH$_2$C$\underline{H}_2$,NCH$_2$C$\underline{H}_2$CH$_2$).

ESI-MS m/z: 456.2(M+H)$^+$.

e) Preparation of (3R,4R,5S)-4-acetamido-5-amino-3-((3S)-3-(2-methoxylethoxyl)piperidin)-1-cyclohexene-1-carboxylic acid trifluoroacetate.

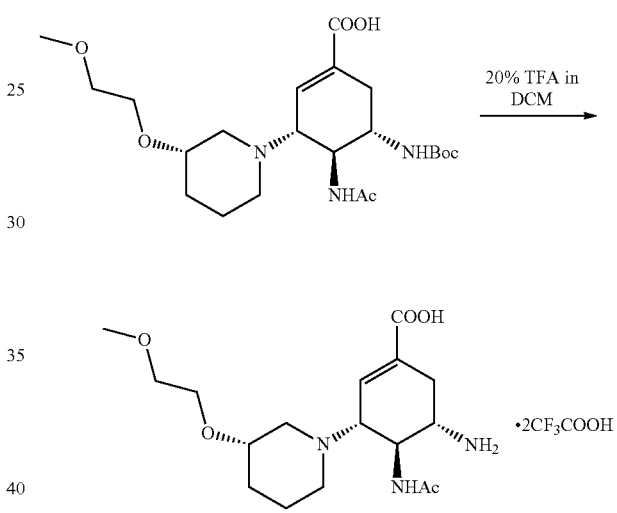

According to the above equation, (3R,4R,5S)-4-acetamido-5-((tert-butyloxycarbonyl) amino)-3-((3S)-3-(2-methoxylethoxyl)piperidin)-1-cyclohexene-1-carboxylic acid was added into a single-neck flask, and 4 mL of DCM and 1 mL of TFA were then added and stirred at room temperature for 1 hour. After the TLC (DCM:MeOH=5:1) indicated that the reaction was completed, the solvent was evaporated to dryness and the residual TFA was removed by using an oil pump. Diethyl ether was added, and filtered out when a solid appears, and a white powder is obtained.

The characterization analysis of the product:

$^1$H-NMR(400 MHz,D$_2$O):δppm6.938(dd,1H,2-C$\underline{H}$),4.696-4.644(dd,1H,4-C$\underline{H}$), 4.457-4.434(dd,1H,3-C$\underline{H}$),3.989-3.980(dd,1H,5-C$\underline{H}$),3.628-3.620(t,2H,OC$\underline{H}_2$CH$_2$O),3.634-3.630(m,1H,NCH$_2$C$\underline{H}$OCH$_2$),3.588-3.572(t,2H, OCH$_2$C$\underline{H}_2$O),3.554-3.536(m,4H,NC$\underline{H}_2$CHOCH$_2$,NC$\underline{H}_2$CH$_2$),3.396(s,3H,OC$\underline{H}_3$), 3.112-3.068(dd,2H,6-C$\underline{H}_2$),2.637-2.266(m,1H, NCH$_2$C$\underline{H}_2$),2.200-2.168(m,2H,NCH$_2$CH$_2$C$\underline{H}_2$,NCH$_2$C$\underline{H}_2$CH$_2$),2.139(s,3H,COC$\underline{H}_3$),1.865-1.831(m,1H,NCH$_2$C$\underline{H}_2$).

ESI-MS m/z: 356.2(M+H)$^+$.

EXAMPLE 2 a) Preparation of ethyl (3R,4S,5S)-4-acetamido-5-azido-3-((3R)-3-(2-methoxylethoxyl)piperidin)-1-cyclohexene-1-carboxylate.

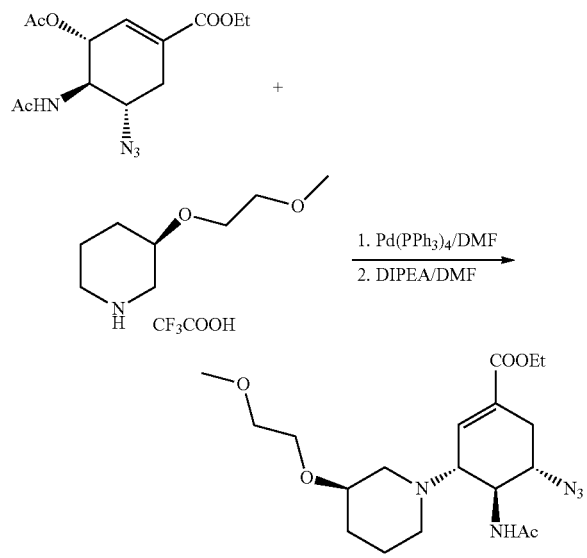

Ethyl (3R,4S,5S)-4-acetamido-5-azido-3-((3R)-3-(2-methoxylethoxyl)piperidin)-1-cyclohexene-1-carboxylate was prepared with reference to the Example 1a).

The characterization analysis of the product:

$^1$-H-NMR(400 MHz,CDCl$_3$):δppm6.837(s,1H,NH),5.715-5.694(dd,1H,2-CH),4.201-4.184(q,2H,CH$_2$CH$_3$),3.925-3.877(dd,1H,4-CH),3.781-3.715(dd,1H,3-CH),3.604-3.530(t,2H,OCH$_2$CH$_2$O),3.502-3.491(m,1H,NCH$_2$CHOCH$_2$),3.490-3.451(t,2H,OCH$_2$CH$_2$O),3.351(s,3H,OCH$_3$),3.282-3.239(d,1H,NCH$_2$CHOCH$_2$),3.016-2.991(t,1H,NCH$_2$CH$_2$),2.893-2.837(t,1H,NCH$_2$CH$_2$),2.529-2.516(m,2H,NCH$_2$CHOCH$_2$,5-CH),2.352-2.285(dd,1H,6-CH$_2$),2.248-2.202(m,1H,NCH$_2$CH$_2$CH$_2$),2.182-2.177(dd,1H,6-CH$_2$),2.061(s,3H,COCH$_3$),1.959-1.935(m,1H,NCH$_2$CH$_2$CH$_2$),1.715-1.760(m,1H,NCH$_2$CH$_2$CH$_2$),1.532-1.423(m,1H,NCH$_2$CH$_2$CH$_2$),1.352-1.330(t,3H,CH$_2$CH$_3$).

ESI-MS m/z: 410.3 (M+H)$^+$.

b) Preparation of ethyl (3R,4R,5S)-4-acetamido-5-amino-3-((3R)-3-(2-methoxylethoxyl)piperidin)-1-cyclohexene-1-carboxylate.

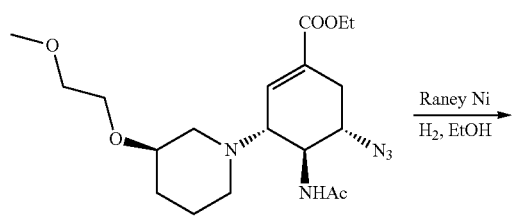

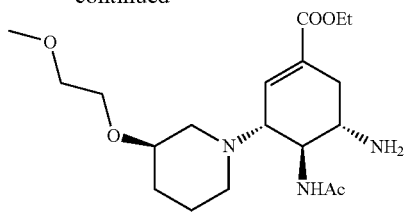

Ethyl (3R,4R,5S)-4-acetamido-5-amino-3-((3R)-3-(2-methoxylethoxyl)piperidin)-1-cyclohexene-1-carboxylate was prepared with reference to Example 1b).

The characterization analysis of the product:

$^1$-H-NMR(400 MHz,CDCl$_3$):δppm6.837(s,1H,NH),5.555-5.534(dd,1H,2-CH),4.206-4.126(q,2H,CH$_2$CH$_3$),3.892-3.818(dd,1H,4-CH),3.655-3.559(t,2H,OCH$_2$CH$_2$O),3.520-3.495(t,2H,OCH$_2$CH$_2$O),3.452-2.430(dd,1H,3-CH),3.395-3.356(s,3H,OCH$_3$),3.295-3.250(dd,1H,5-CH),3.249-3.210(m,1H,NCH$_2$CHOCH$_2$),3.021-2.999(d,1H,NCH$_2$CHOCH$_2$),2.925-2.883(t,1H,NCH$_2$CH$_2$),2.870-2.857(t,1H,NCH$_2$CH$_2$),2.615-2.570(d,1H,NCH$_2$CHOCH$_2$),2.544-2.517(dd,1H,6-CH$_2$),2.165-2.155(dd,1H,6-CH$_2$),2.142-2.118(m,1H,NCH$_2$CH$_2$CH$_2$),2.044(s,3H,COCH$_3$),1.949-1.920(m,1H,NCH$_2$CH$_2$CH$_2$),1.714-1.704(m,1H,NCH$_2$CH$_2$CH$_2$),1.525-1.400(m,1H,NCH$_2$CH$_2$CH$_2$),1.3

ESI-MS m/z: 384.2(M+H)$^+$.

c) Preparation of ethyl (3R,4R,5S)-4-acetamido-5-((tert-butyloxycarbonyl) amino)-3-((3R)-3-(2-methoxylethoxyl)piperidin)-1-cyclohexene-1-carboxylate.

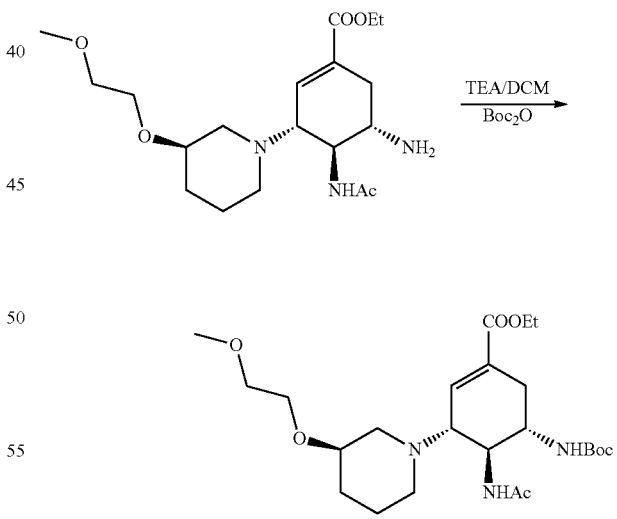

Ethyl (3R,4R,5S)-4-acetamido-5-((tert-butyloxycarbonyl) amino)-3-((3R)-3-(2-methoxylethoxyl)piperidin)-1-cyclohexene-1-carboxylate was prepared with reference to Example 1 c). ESI-MS m/z for the product: 484.2(M+H)$^+$.

d) Preparation of (3R,4R,5S)-4-acetamido-5-((tert-butyloxycarbonyl) amino)-3-((3R)-3-(2-methoxylethoxyl)piperidin)-1-cyclohexene-1-carboxylic acid.

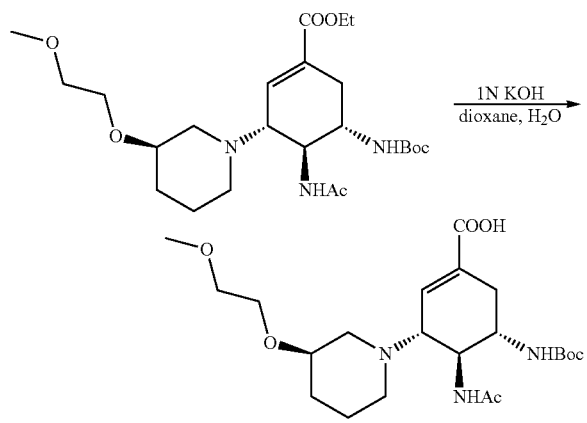

(3R,4R,5S)-4-acetamido-5-((tert-butyloxycarbonyl) amino)-3-((3R)-3-(2-methoxylethoxyl)piperidin)-1-cyclohexene-1-carboxylic acid was prepared with reference to Example 1 d).

The characterization analysis of the product:
¹H-NMR(400 MHz,MeOD):δppm6.751(dd,1H,2-CH̲),5.491(s,1H,NH̲)4.070-4.019(dd,1H,4-CH̲),3.693-3.680(dd,1H,5-CH̲),3.632-3.621(t,2H,OCH₂CH̲₂O),3.526-3.516(t,2H,OCH̲₂CH₂O),3.480-3.460(dd,1H,3-CH̲),3.357(s,3H,OCH̲₃),3.181-3.156(m,1H,NCH₂CH̲OCH₂),2.796-2.760(d,1H,NCH̲₂CHOCH₂),2.750-2.689(m,2H,NCH̲₂CH₂,NCH̲₂CHOCH₂),4.485-2.396(dd,1H,6-CH̲₂),2.249-2.176(t,1H,NCH̲₂CH₂),1.976(s,3H,COCH̲₃),1.903-1.883 (dd,1H,6-CH̲₂),1.850-1.796(m,1H,NCH₂CH₂CH̲₂),1.555-1.540(m,2H,NCH₂CH₂CH̲₂,NCH₂CH̲₂CH₂),1.444(s,9H,C(CH̲₃)₃), 1.380-1.372(m,1H,NCH₂CH̲₂CH₂).
ESI-MS m/z: 456.2(M+H)⁺.

e) Preparation of (3R,4R,5S)-4-acetamido-5-amino-3-((3R)-3-(2-methoxyethoxyl)piperidin)-1-cyclohexene-1-carboxylic acid trifluoroacetate.

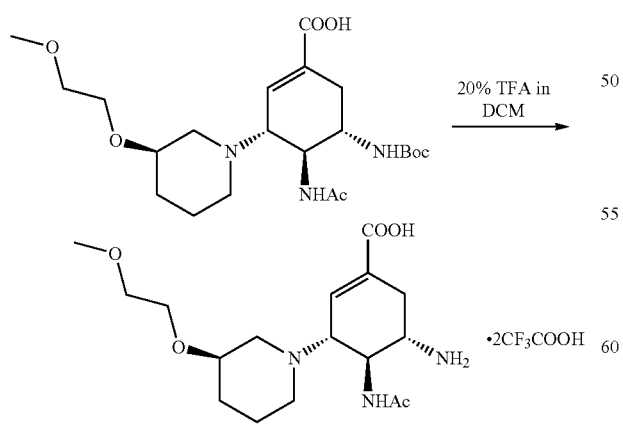

(3R,4R,5S)-4-acetamido-5-amino-3-((3R)-3-(2-methoxylethoxyl)piperidin)-1-cyclohexene-1-carboxylic acid trifluoroacetate was prepared with reference to Example 1 e).

The characterization analysis of the product:
¹H-NMR(400 MHz,D₂O):δppm6.942(dd,1H,2-CH̲),4.689-4.642(dd,1H,4-CH̲), 4.463-4.445(dd,1H,3-CH̲),3.995-3.899(dd,1H,5-CH̲),3.678-3.645(t,2H,OCH̲₂CH₂O),3.692-3.663(m,1H,NCH₂CH̲OCH₂),3.602-3.588(t,2H,OCH₂CH̲₂O),3.562-3.532(m,4H,NCH̲₂CHOCH₂,NCH̲₂CH₂),3.401(s,3H,OCH̲₃),3.121-3.108(dd,2H,6-CH̲₂),2.645-2.285(m,1H,NCH̲₂CH₂CH̲₂),2.301-2.178(m,2H,NCH₂CH₂CH̲₂,NCH₂CH̲₂CH₂),2.146(s,3H,COCH̲₃),1.876-1.850(m,1H, NCH₂CH̲₂CH₂).
ESI-MS m/z: 356.2(M+H)⁺.

EXAMPLE 3 a) Preparation of ethyl (3R,4S,5S)-4-acetamido-5-azido-3-((3S)-3-(2-hydroxyethoxyl)piperidin)-1-cyclohexene-1-carboxylate.

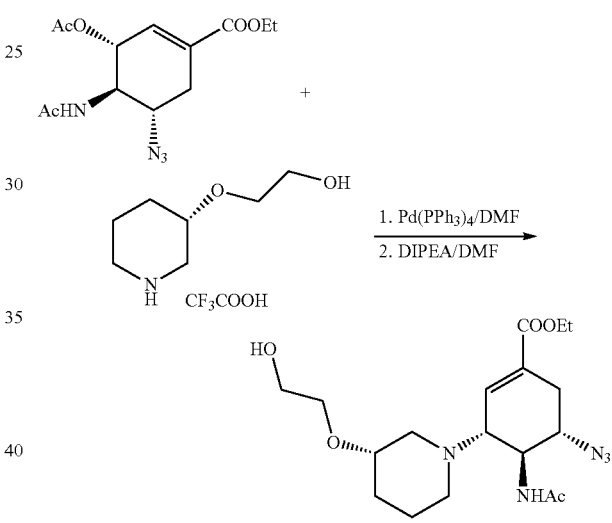

Ethyl (3R,4S,5S)-4-acetamido-5-azido-3-((3S)-3-(2-hydroxyethoxyl)piperidin)-1-cyclohexene-1-carboxylate was prepared with reference to t Example 1 a).

The characterization analysis of the product:
¹H-NMR(400 MHz,CDCl₃):δppm6.869(s,1H,NH̲),5.561-5.539(dd,1H,2-CH̲), 4.255-4.193(q,2H,COOCH̲₂CH₃),4.014-3.940(dd,1H,4-CH̲),3.834-3.193(m,2H,OCH̲₂CH̲₂OH),3.702-3.635(m,2H,OCH̲₂CH₂OH),3.419-3.395(dd,1H,3-CH̲),2.958-2.943(m,1H,NCH₂CH̲),2.914-2.900(m,1H,NCH̲₂CH),2.787-2.750(m,1H,NCH̲₂CH₂),2.711-2.661(m,1H,NCH̲₂CH₂),2.585-2.261(m,1H,NCH̲₂CH),2.554-2.534(m,1H,5-CH̲),2.332-2.262(m,1H,6-CH̲₂),2.071(s,3H,COCH̲₃),1.846-1.811(m,2H,NCH₂CH̲₂CH̲₂),1.507-1.466(m,2H, NCH₂CH̲₂CH̲₂),1.329-1.295(t,3H, COOCH₂CH̲₃).
ESI-MS m/z: 396.2 (M+H)⁺.

b) Preparation of ethyl (3R,4S,5S)-4-acetamido-5-amino-3-((3S)-3-(2-hydroxyethoxyl)piperidin)-1-cyclohexene-1-carboxylate.

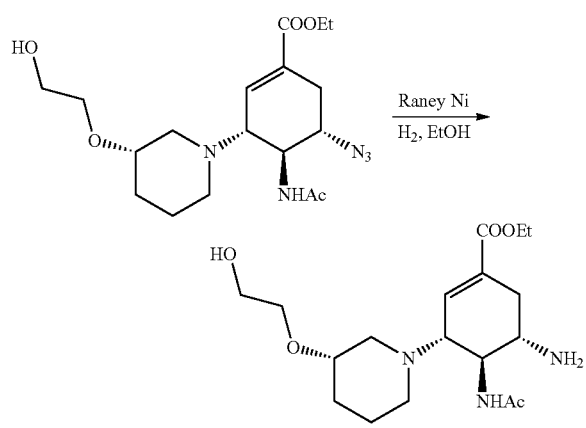

Ethyl (3R,4S,5S)-4-acetamido-5-amino-3-((3S)-3-(2-hydroxyethoxyl)piperidin)-1-cyclohexene-1-carboxylate was prepared with reference to Example 1 b). The characterization analysis of the product: ESI-MS m/z: 370.2 (M+H)+.

c) Preparation of ethyl (3R,4R,5S)-4-acetamido-5-((tert-butyloxycarbonyl) amino)-3-((3S)-3-(2-hydroxyethoxyl)piperidin)-1-cyclohexene-1-carboxylate.

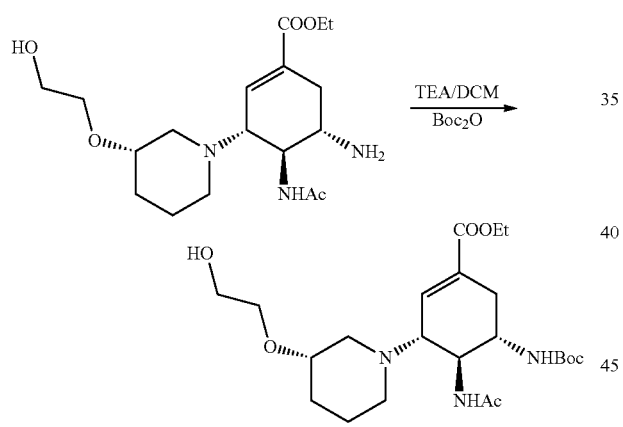

Ethyl (3R,4R,5S)-4-acetamido-5-((tert-butyloxycarbonyl) amino)-3-((3S)-3-(2-hydroxyethoxyl)piperidin)-1-cyclohexene-1-carboxylate was prepared with reference to Example 1 c). The characterization analysis of the product: ESI-MS m/z for the product: 470.2 (M+H)+.

d) Preparation of (3R,4R,5S)-4-acetamido-5-((tert-butyloxycarbonyl) amino)-3-((3S)-3-(2-hydroxyethoxyl)piperidin)-1-cyclohexene-1-carboxylic acid.

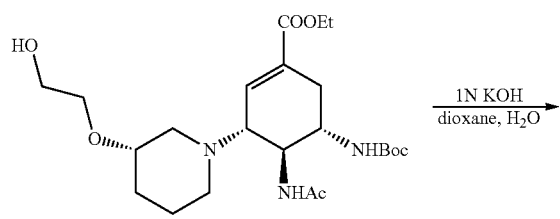

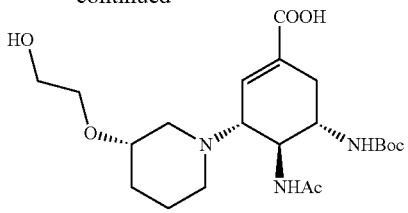

(3R,4R,5S)-4-acetamido-5-((tert-butyloxycarbonyl) amino)-3-((3S)-3-(2-hydroxyethoxyl)piperidin)-1-cyclohexene-1-carboxylic acid was prepared with reference to Example 1 d). The characterization analysis of the product: 442.2 (M+H)+.

e) Preparation of (3R,4R,5S)-4-acetamido-5-amino-3-((3S)-3-(2-hydroxyethoxyl)piperidin)-1-cyclohexene-1-carboxylic acid trifluoroacetate.

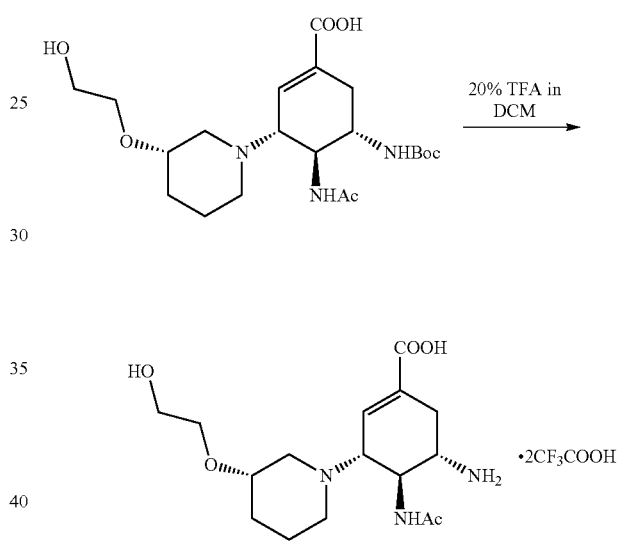

(3R,4R,5S)-4-acetamido-5-amino-3-((3S)-3-(2-hydroxyethoxyl)piperidin)-1-cyclohexene-1-carboxylic acid trifluoroacetate was prepared with reference to Example 1 e).

The characterization analysis of the product:

$^1$H-NMR(400 MHz, CDCl):δppm6.993(dd,1H,2-C$\underline{H}$),4.401-4.354(dd,1H,4-C$\underline{H}$), 4.027-3.981(dd, 1H,3-C$\underline{H}$),3.612-3.462(m,2H,OCH$_2$C$\underline{H}_2$OH),3.352-3.343(m,2H,OC$\underline{H}_2$CH$_2$OH),3.289-3.165(m,1H,5-C$\underline{H}$),3.046-3.019(m,1H,NCH$_2$C$\underline{H}$),2.952-2.898(m,2H,NC$\underline{H}_2$CH,NCH$_2$CH$_2$),2.856-2.804(m,1H,NC$\underline{H}_2$CH$_2$),2.763-2.649(m,1H,NC$\underline{H}_2$CH),2.465-2.381(m,2H,6-C$\underline{H}_2$),2.082(s,3H,COC$\underline{H}_3$),1.861-1.831(m,1H,NCH$_2$CH$_2$C$\underline{H}_2$),1.726-1.705(m,1H,NCH$_2$C$\underline{H}_2$CH$_2$),1.616-1.559(m,1H,NCH$_2$CH$_2$C$\underline{H}_2$),1.312-1.286(m,1H,NCH$_2$C$\underline{H}_2$CH$_2$).

ESI-MS m/z: 342.2 (M+H)+.

EXAMPLE 4 a) Preparation of ethyl (3R,4S,5S)-4-acetamido-5-azido-3-((3S)-3-(2-ethoxyethoxyl)piperidin)-1-cyclohexene-1-carboxylate.

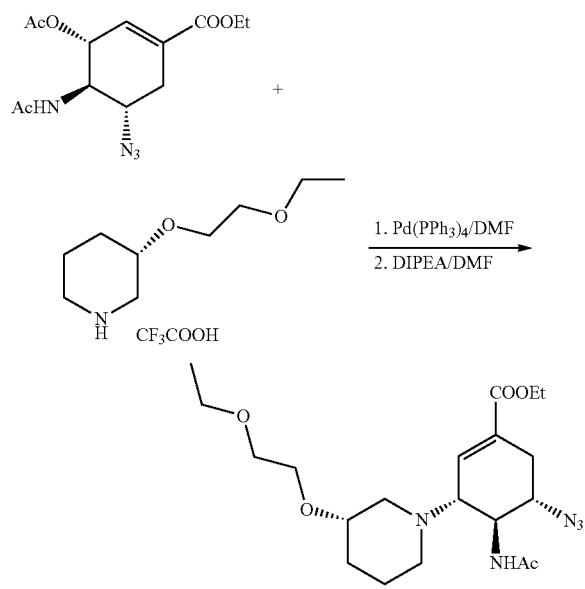

Ethyl (3R,4S,5S)-4-acetamido-5-azido-3-((3S)-3-(2-ethoxylethoxyl)piperidin)-1-cyclohexene-1-carboxylate was prepared with reference to Example 1 a). The characterization analysis of the product: ESI-MS m/z: 448.2 (M+H)+.

b) Preparation of ethyl (3R,4S,5S)-4-acetamido-5-amino-3-((3S)-3-(2-ethoxylethoxyl)piperidin)-1-cyclohexene-1-carboxylate.

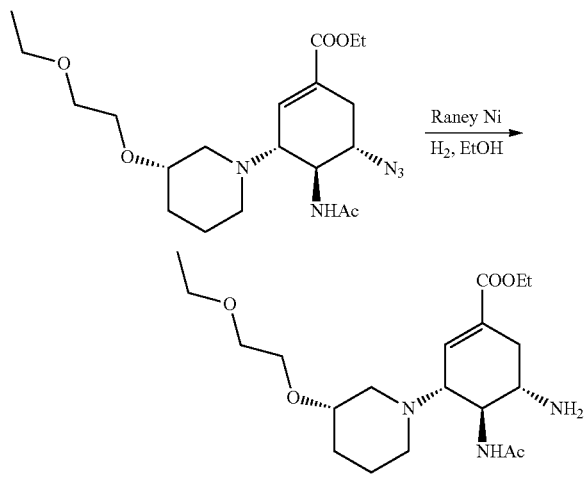

Ethyl (3R,4S,5S)-4-acetamido-5-amino-3-((3S)-3-(2-ethoxylethoxyl)piperidin)-1-cyclohexene-1-carboxylate was prepared with reference to Example 1 b). The characterization analysis of the product: ESI-MS m/z: 398.3 (M+H)+.

c) Preparation of ethyl (3R,4S,5S)-4-acetamido-5-((tert-butyloxycarbonyl) amino)-3-((3S)-3-(2-ethoxyethoxyl)piperidin)-1-cyclohexene-1-carboxylate.

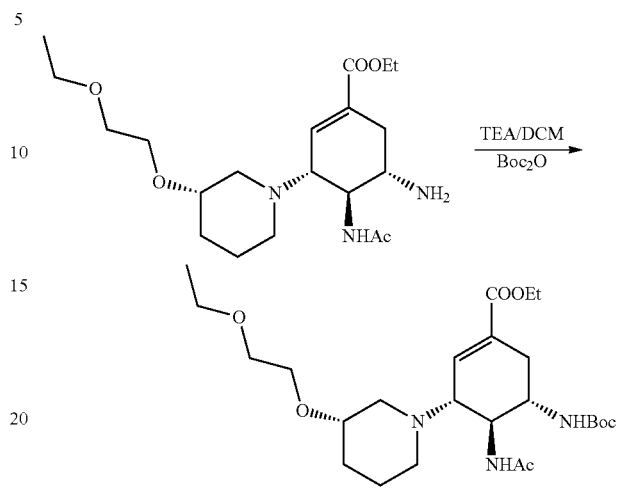

Ethyl (3R,4S,5S)-4-acetamido-5-((tert-butyloxycarbonyl) amino)-3-((3S)-3-(2-ethoxylethoxyl)piperidin)-1-cyclohexene-1-carboxylate was prepared with reference to Example 1 c). The characterization analysis of the product: ESI-MS m/z: 522.2 (M+H)+.

d) Preparation of (3R,4S,5S)-4-acetamido-5-((tert-butyloxycarbonyl) amino)-3-((3S)-3-(2-ethoxylethoxyl)piperidin)-1-cyclohexene-1-carboxylic acid.

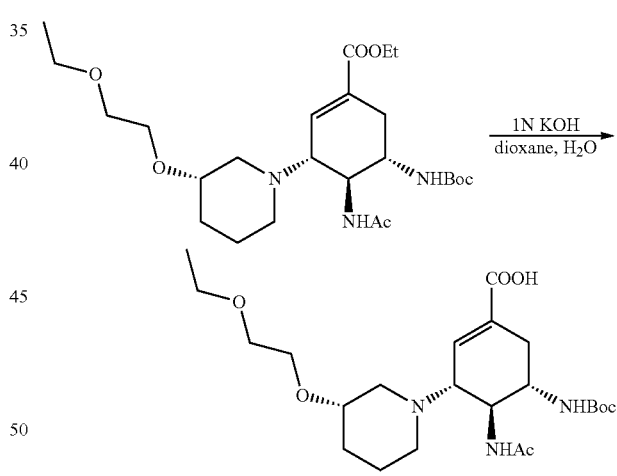

(3R,4S,5S)-4-acetamido-5-((tert-butyloxycarbonyl) amino)-3-((3S)-3-(2-ethoxylethoxyl)piperidin)-1-cyclohexene-1-carboxylic acid was prepared with reference to Example 1 d).

The characterization analysis of the product:
1-H-NMR(400 MHz,CDCl$_3$):δppm6.892(dd,1H,2-C$\underline{H}$),5.421-5.335(dd,1H,4-C$\underline{H}$), 4.165-4.046(dd,1H,5-C$\underline{H}$),3.769-3.745(m,1H,3-C$\underline{H}$),5.542-3.483(m,6H,OC$\underline{H}_2$C$\underline{H}_2$O,CH$_2$OC$\underline{H}_2$CH3),3.392-3.856(m,1H,NCH$_2$C$\underline{H}$),2.932-2.865(m,1H,NC$\underline{H}_2$CH),2.812-2.745(m,2H,NC$\underline{H}_2$CH$_2$),2.545-5.465(m, 1H,6-C$\underline{H}_2$),2.389-2.275(m,1H,NC$\underline{H}_2$CH),2.254-2.178(m,1H,6-C$\underline{H}_2$),1.985(s,3H,COC$\underline{H}_3$),1.954-1.938(m,1H,NCH$_2$C$\underline{H}_2$C$\underline{H}_2$),1.713-1.645(m,2H,NCH$_2$CH$_2$C$\underline{H}_2$NCH$_2$C H̱₂CH₂),1.420(s,9H,C(CH̱₃)₃),1.398-1.252(m,1H,NCH₂CH̱₂CH₂),1.191-1.156(t,3H, CH₂OCH₂CH̱₃).

ESI-MS m/z for the product: 470.3 (M+H)⁺.

e) Preparation of (3R,4S,5S)-4-acetamido-5-amino-3-((3S)-3-(2-ethoxylethoxyl)piperidin)-1-cyclohexene-1-carboxylic acid trifluoroacetate.

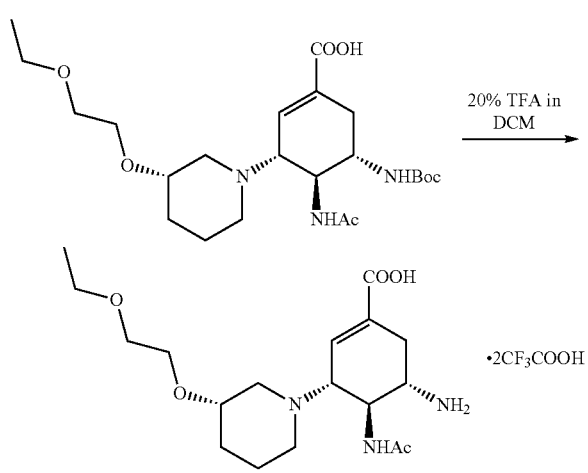

(3R,4S,5S)-4-acetamido-5-amino-3-((3S)-3-(2-ethoxylethoxyl)piperidin)-1-cyclohexene-1-carboxylic acid trifluoroacetate was prepared with reference to Example 1 e).

The characterization analysis of the product:
¹H-NMR(400 MHz,CDCl₃):δppm7.002(dd,1H,2-CH̱),4.498-4.389(dd,1H,4-CH̱), 3.746-3.694(m,1H,3-CH̱),3.625-3.534(m,4H₂OCH̱₂CH̱₂O),3.398-3.376(m,2H,CH₂OCH̱₂CH₃),3.201-3.194(dd,1H,5-CH̱),3.078-3.054(m, 1H,NCH₂CH̱),3.042-3.201(m,1H,NCH̱₂CH),2.964-2.945(m,2H,NCH̱₂CH₂),2.879-2.850(m,1H,6-CH̱₂),2.539-2.502(m,1H,NCH̱₂CH),2.105-2.098(m,1H,6-CH̱₂),2.090(s,3H,COCH̱₃),1.879-1.786(m,2H,NCH₂CH₂CH̱₂NCH₂CH̱₂CH2),1.726-1.649(m,2H,NCH₂CH₂CH̱₂NCH₂CH̱₂CH₂),1.219-1.184(t,3H, CH₂OCH₂CH̱₃) ESI-MS m/z: 370.3 (M+H)⁺.

EXAMPLE 5 a) Preparation of ethyl (3R,4S,5S)-4-acetamido-5-azido-3-((3S)-3-((2-(cyclopropylmethoxyl)ethoxyl)piperidin)-1-cyclohexene-1-carboxylate.

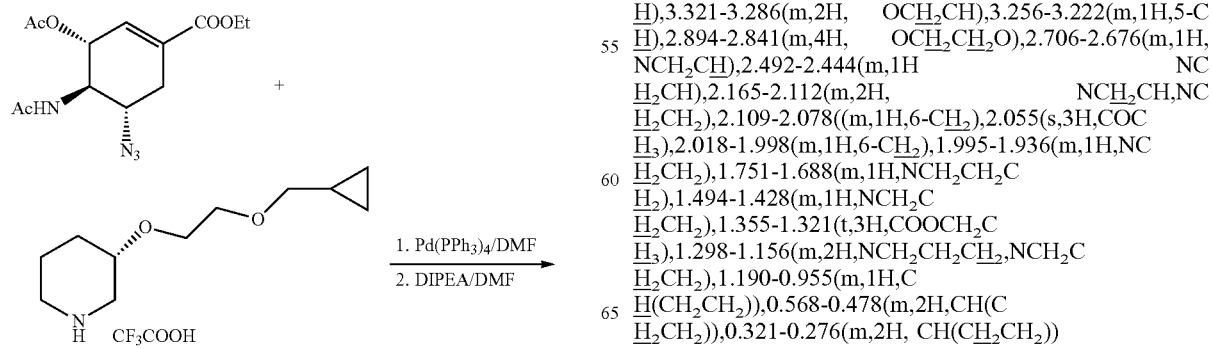

Ethyl (3R,4S,5S)-4-acetamido-5-azido-3-((3S)-3-((2-(cyclopropylmethoxyl)ethoxyl)piperidin)-1-cyclohexene-1-carboxylate was prepared with reference to Example 1 a).

The characterization analysis of the product: ESI-MS m/z: 450.3 (M+H)⁺.

b) Preparation of ethyl (3R,4S,5S)-4-acetamido-5-amino-3-((3S)-3- ((2-(cyclopropylmethoxyl)ethoxyl)piperidin)-1-cyclohexene-1-carboxylate.

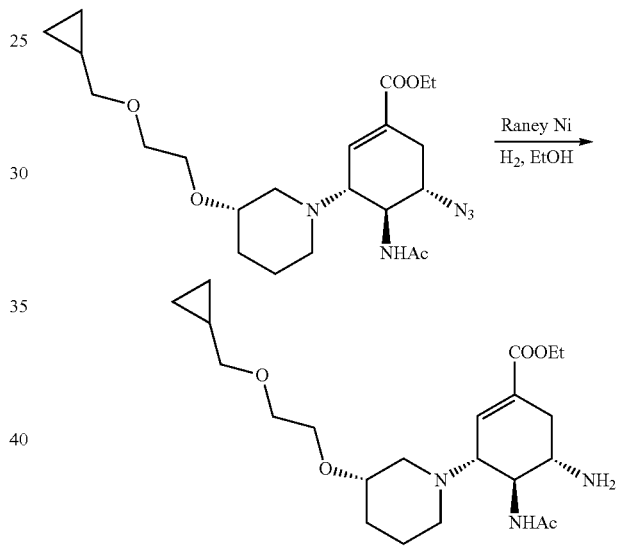

Ethyl (3R,4S,5S)-4-acetamido-5-amino-3-((3S)-3-((2-(cyclopropylmethoxyl)ethoxyl)piperidin)-1-cyclohexene-1-carboxylate was prepared with reference to Example 1 b).

The characterization analysis of the product:
¹H-NMR(400 MHz,CDCl₃):δppm6.898(s,1H,NH̱),5.497-5.446(dd,1H,2-CH̱), 4.214-4.169(q,2H,COOCH̱₂CH₃),3.868-3.795(dd,1H,4-CH̱),3.401-3.369(m,1H,3-CH̱),3.321-3.286(m,2H, OCH̱₂CH),3.256-3.222(m,1H,5-CH̱),2.894-2.841(m,4H, OCH̱₂CH̱₂O),2.706-2.676(m,1H, NCH₂CH̱),2.492-2.444(m,1H NCH̱₂CH),2.165-2.112(m,2H, NCH̱₂CH,NCH̱₂CH₂),2.109-2.078((m,1H,6-CH̱₂),2.055(s,3H,COCH̱₃),2.018-1.998(m,1H,6-CH̱₂),1.995-1.936(m,1H,NCH̱₂CH₂),1.751-1.688(m,1H,NCH₂CH₂CH̱₂),1.494-1.428(m,1H,NCH₂CH̱₂CH₂),1.355-1.321(t,3H,COOCH₂CH̱₃),1.298-1.156(m,2H,NCH₂CH₂CH̱₂,NCH₂CH̱₂CH₂),1.190-0.955(m,1H,CH̱(CH₂CH₂)),0.568-0.478(m,2H,CH(CH̱₂CH₂)),0.321-0.276(m,2H, CH(CH̱₂CH₂))

ESI-MS m/z: 424.3 (M+H)⁺.

c) Preparation of ethyl (3R,4S,5S)-4-acetamido-5-((tert-butyloxycarbonyl) amino)-3-((3S)-3-((2-(cyclopropylmethoxyl)ethoxyl)piperidin)-1-cyclohexene-1-carboxylate.

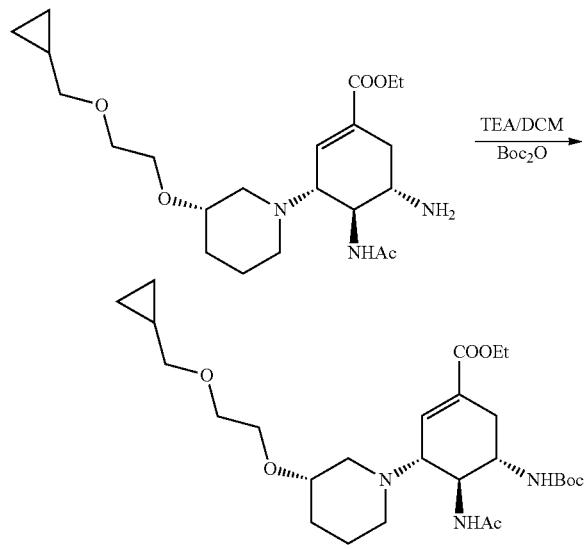

Ethyl (3R,4S,5S)-4-acetamido-5-((tert-butyloxycarbonyl) amino)-3-((3S)-3-((2-(cyclopropylmethoxyl)ethoxyl)piperidin)-1-cyclohexene-1-carboxylate was prepared with reference to Example 1 c).

The characterization analysis of the product: ESI-MS m/z: 524.3 (M+H)$^+$.

d) Preparation of (3R,4S,5S)-4-acetamido-5-((tert-butyloxycarbonyl) amino)-3-((3S)-3-((2-(cyclopropylmethoxy)ethoxyl)piperidin)-1-cyclohexene-1-carboxylic acid.

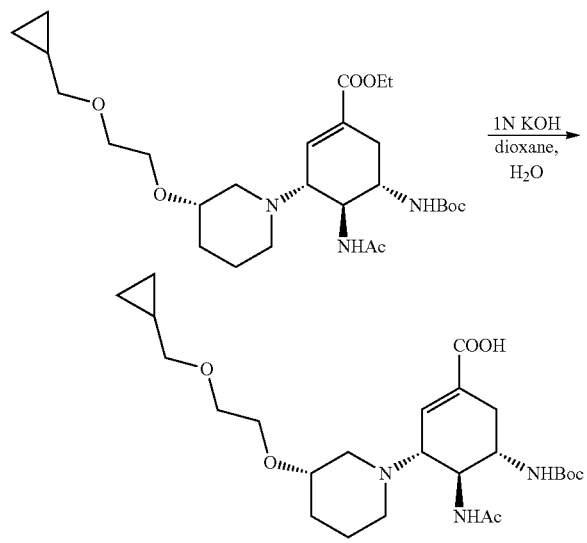

(3R,4S,5S)-4-acetamido-5-((tert-butyloxycarbonyl) amino)-3-((3S)-3-((2-(cyclopropylmethoxyl)ethoxyl)piperidin)-1-cyclohexene-1-carboxylic acid was prepared with reference to Example 1 d).

The characterization analysis of the product:
$^1$H-NMR(400 MHz,CDCl$_3$):δppm6.887(dd,1H,2-CH),5.446-5.426(dd,1H,4-CH), 4.211-4.189(m,1H,5-CH),3.946-3.932(m,1H,3-CH),3.794-3.782(m,2H,OCH$_2$CH$_2$O),3.869-3.659(m,2H,OCH$_2$CH$_2$O),3.336-3.320(m,2H,OCH$_2$CH),3.623-3.116(m,1H,NCH$_2$CH),3.099-3.036(m,2H,NCH$_2$CH,NCH$_2$CH$_2$),2.926-2.886(m,1H,NCH$_2$CH),2.846-2.827(m,1H,6-CH$_2$),2.389-3.313(m,1H,NCH$_2$CH),2.073-2.066(m,1H,6-CH$_2$),2.039-2.017(s,3H,COCH$_3$),1.956-1.935(m,1H,NCH$_2$CH$_2$CH$_2$),1.726-1.635(m,2H,NCH$_2$CH$_2$CH$_2$,NCH$_2$CH$_2$CH2),1.421(s,9H,C(CH$_3$)$_3$),1.864-1.031(m,1H,NCH$_2$CH$_2$),0.899-0.836(m,1H,CH(CH$_2$CH$_2$)),0.527-0.507(m,2H,CH(CH$_2$CH$_2$)),0.215-0.204(m,2H,CH(CH$_2$CH$_2$)).

ESI-MS m/z: 494.2 (M+H)$^+$.

e) Preparation of (3R,4S,5S)-4-acetamido-5-amino-3-((3S)-3-((2-(cyclopropylmethoxyl)ethoxyl)piperidin)-1-cyclohexene-1-carboxylic acid trifluoroacetate.

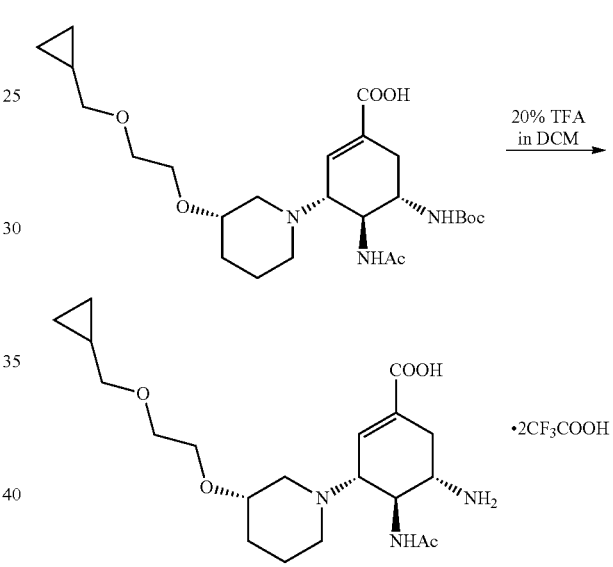

(3R,4S,5S)-4-acetamido-5-amino-3-((3S)-3-((2-(cyclopropylmethoxy)ethoxyl)piperidin)-1-cyclohexene-1-carboxylic acid trifluoroacetate was prepared with reference to Example 1 e).

The characterization analysis of the product:
$^1$H-NMR(400 MHz,MeOD):δppm6.996(dd,1H,2-CH),4.403-4.354(dd,1H,4-CH), 4.089-4.021(m,1H,3-CH),3.721-3.675(m,2H,OCH$_2$CH$_2$O),3.601-3.516(m,2H,OCH$_2$CH$_2$O),3.458-3.976(m,1H,5-CH),3.388-3.380(m,2H,OCH$_2$CH),3.357-3.349(m,1H,NCH$_2$CH),3.340-3.310(m,2H,NCH$_2$CH,NCH$_2$CH$_2$),3.287-3.176(m,1H,NCH$_2$CH),3.123-3.087(m,1H,6-CH$_2$),3.047-3.015(m,1H,NCH$_2$CH),2.524-2.455(m,1H,6-CH$_2$),2.086(s,3H,COCH$_3$),2.047-2.018(m,1H,NCH$_2$CH$_2$),1.876-1.816(m,1H,NCH$_2$CH$_2$),1.689-1.615(m,2H,NCH$_2$CH$_2$CH$_2$,NCH$_2$CH$_2$),1.056-1.027(m,1H,CH(CH$_2$CH$_2$)),0.549-0.518(m,2H,CH(CH$_2$CH$_2$)),0.243-0.219(m,2H,CH(CH$_2$CH$_2$)).

ESI-MS m/z: 394.2 (M+H)$^+$.

EXAMPLE 6 a) Preparation of ethyl (3R,4S,5S)-4-acetamido-5-azido-3-((3S)-3-((2-(methoxylethoxyl)methyl)piperidin)-1-cyclohexene-1-carboxylate.

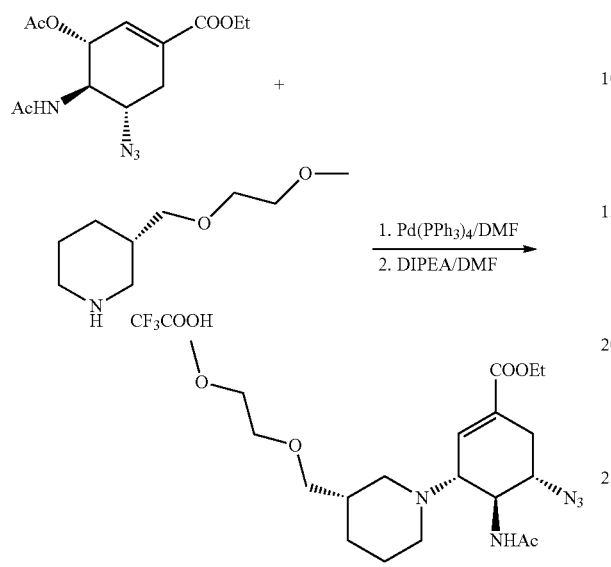

Ethyl (3R,4S,5S)-4-acetamido-5-azido-3-((3S)-3-((2-(methoxylethoxyl)methyl)piperidin)-1-cyclohexene-1-carboxylate was prepared with reference to Example 1 a).

The characterization analysis of the above product: ESI-MS m/z: 448.2(M+H)+.

b) Preparation of ethyl (3R,4S,5S)-4-acetamido-5-amino-3-((3S)-3-((2-(methoxylethoxyl)methyl)piperidin)-1-cyclohexene-1-carboxylate.

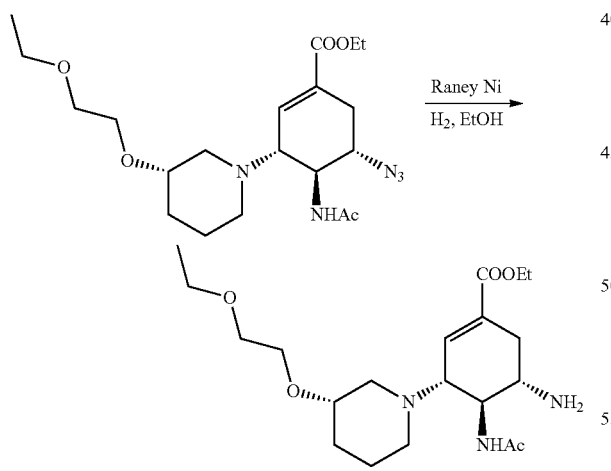

Ethyl (3R,4S,5S)-4-acetamido-5-amino-3-((3S)-3-((2-(methoxyethoxyl)methyl)piperidin)-1-cyclohexene-1-carboxylate was prepared with reference to Example 1 b).

The characterization analysis of the product:
$^1$H-NMR(400 MHz,CDCl$_3$):δppm6.880(s,1H,NH),5.763-5.742(dd,1H,2-CH), 4.200-4.138(m,2H,COOCH$_2$CH$_3$),4.125-4.089(dd,1H,4-CH),3.805-3.757(dd,1H,3-CH),3.554-3.506(m,4H,OCH$_2$CH$_2$O),3.352(s,3H,CH$_2$OCH$_3$),3.328-3.316(m,1H,5-CH),3.282-3.219(m,2H,CH$_2$OCH$_2$CH$_2$),2.874-2.812(m,2H,NCH$_2$CH$_2$),2.757-2.724(m,2H,NCH$_2$CH,6-CH$_2$),2.359.2.309(m,1H,NCH$_2$CH),2.170-2.121(m,1H,6-CH$_2$),2.097(s,3H,COCH$_3$),1.967-1.856(m,1H,NCH$_2$CH),1.623-1.565(m,2H,NCH$_2$CH$_2$CH$_2$,NCH$_2$CH$_2$CH$_2$),1.422-1.336(m,1H,NCH$_2$CH$_2$CH$_2$),1.278-1.215(t,3H,COOCH$_2$CH$_3$),1.021-0.916(m,1H,NCH$_2$CH$_2$CH$_2$).
ESI-MS m/z: 398.2 (M+H)$^+$.

c) Preparation of ethyl (3R,4S,5S)-4-acetamido-5-((tert-butyloxycarbonyl) amino)-3-((3S)-3-((2-(methoxylethoxyl)methyl)piperidin)-1-cyclohexene-1-carboxylate.

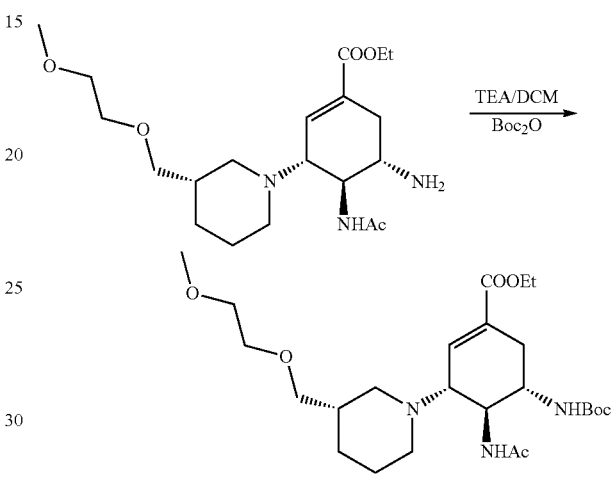

Ethyl (3R,4S,5S)-4-acetamido-5-((tert-butyloxycarbonyl) amino)-3-((3S)-3-((2-(methoxylethoxyl)methyl)piperidin)-1-cyclohexene-1-carboxylate was prepared with reference to Example 1 c).

The characterization analysis of the product: ESI-MS m/z: 498.2 (M+H)$^+$.

d) Preparation of (3R,4S,5S)-4-acetamido-5-((tert-butyloxycarbonyl) amino)-3-((3S)-3-((2-(methoxylethoxyl)methyl)piperidin)-1-cyclohexene-1-carboxylic acid.

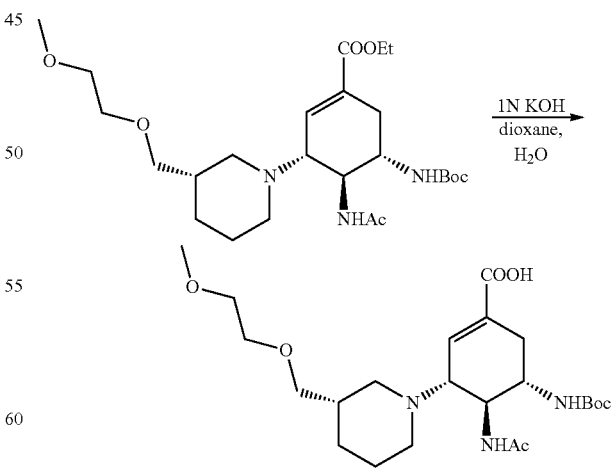

(3R,4S,5S)-4-acetamido-5-((tert-butyloxycarbonyl) amino)-3-((3S)-3-((2-(methoxylethoxyl)methyl)piperidin)-1-cyclohexene-1-carboxylic acid was prepared with reference to Example 1 d).

The characterization analysis of the product:

¹H-NMR(400 MHz,MeOD):δppm6.847(dd,1H,2-CH),5.406-5.372(dd,1H,4-CH), 4.144-4.091(m,1H,5-CH),3.743-3.728(m,1H,3-CH),3.543-3.370(m,4H,OCH₂CH₂O), 3.370(s,3H,CH₂OCH₃),3.324-3.283 (m,1H,CH₂OCH₂CH₂),3.056-2.905 (m,1H,CH₂OCH₂CH₂),2.895-2.873(m,1H,NCH₂CH₂),2.861-2.821(m,1H,NCH₂CH₂),2.589-2.457(m,1H,NCH₂CH),2.436-2.356(m,1H,6-CH₂),2.199-2.186(m,1H,NCH₂CH), 2.125-2.072(m,1H,6-CH₂),1.978(s,3H,COCH₃),1.721-1.686(m,1H,NCH₂CH),1.654-1.556(m,2H,NCH₂CH₂CH₂,NCH₂CH₂CH₂),1.415(s,9H,C(CH₃)3),1.315-1.271(m,1H,NCH₂CH₂CH₂),1.071-1.050(m,1H,NCH₂CH₂CH₂).

ESI-MS m/z for the product: 470.2 (M+H)⁺.

e) Preparation of (3R,4S,5S)-4-acetamido-5-amino-3-((3S)-3-((2-(methoxyethoxyl)methyl)piperidin)-1-cyclohexene-1-carboxylic acid trifluoroacetate.

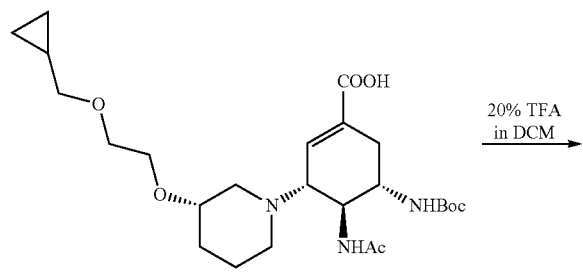

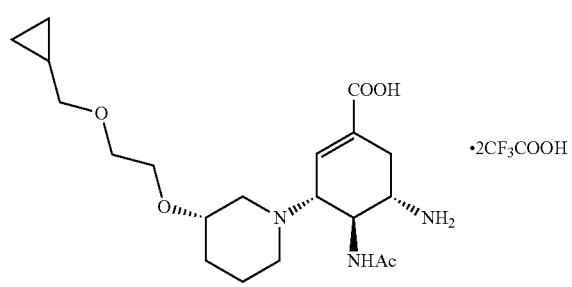

(3R,4S,5S)-4-acetamido-5-amino-3-((3S)-3-((2-(methoxyethoxyl)methyl)piperidin)-1-cyclohexene-1-carboxylic acid trifluoroacetate was prepared with reference to Example 1 e).

The characterization analysis of the product:

¹H-NMR(400 MHz,MeOD):δppm6.969(dd,1H,2-CH),4.469-4.419(dd,1H,4-CH), 4.290-4.286(m,1H,3-CH),3.598-3.512(m,4H₂OCH₂CH₂O),3.495-3.461(m,2H,CH₂OCH₂CH₂),3.359(s,3H,CH₂OCH₃),3.082-3.070(m,1H,5-CH),3.039-3.025(m,1H,NCH₂CH₂),2.886-2.765 (m,1H,NCH₂CH₂),2.529-2.457(m,1H,NCH₂CH),2.445-2.436(m,1H,6-CH₂),2.286-2.175(m,1H,NCH₂CH),2.138-2.086(m, 1H,6-CH₂),1.992(s,3H,COCH₃),1.821-1.765(m,1H,NCH₂CH),1.721-1.665(m,2H,NCH₂CH₂CH₂,NCH₂CH₂CH₂),1.421-1.335(m,1H,NCH₂CH₂CH₂),1.213-1.159(m,1H,NCH₂CH₂CH₂).

ESI-MS m/z: 370.2(M+H)⁺.

EXAMPLE 7 a) Preparation of ethyl (3R,4S,5S)-4-acetamido-5-azido-3-((3S)-3-((2-(ethoxylcarbonyl)amino)ethoxyl)piperidin)-1-cyclohexene-1-carboxylate.

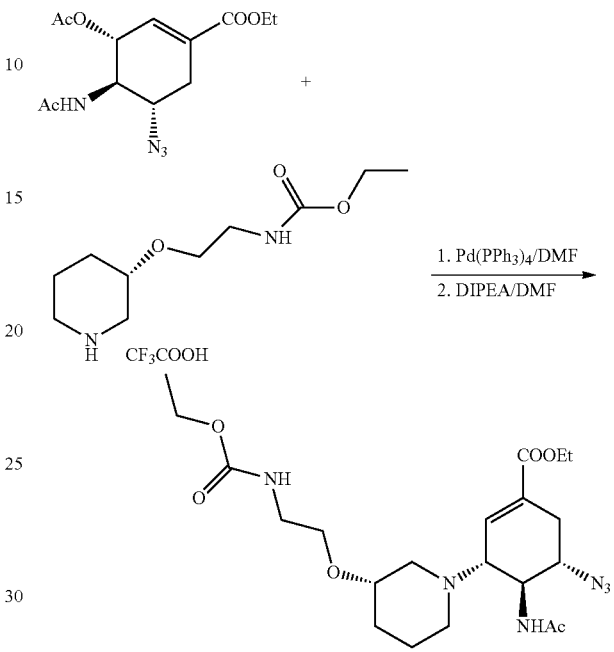

Ethyl (3R,4S,5S)-4-acetamido-5-azido-3-((3S)-3-((2-(ethoxylcarbonyl)amino)ethoxyl)piperidin)-1-cyclohexene-1-carboxylate was prepared with reference to Example 1 a). The characterization analysis of the product: ESI-MS m/z: 467.2 (M+H)⁺.

b) Preparation of ethyl (3R,4S,5S) -4-acetamido-5-amino-3-((3S)-3-((2-(ethoxylcarbonyl)amino)ethoxyl)piperidin)-1-cyclohexene-1-carboxylate.

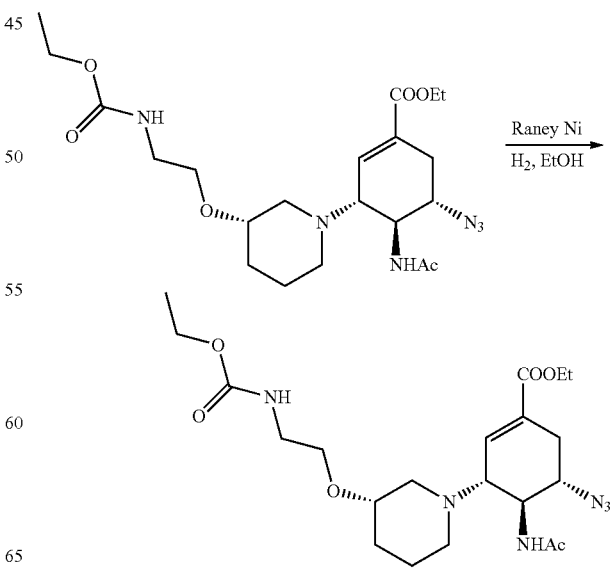

Ethyl (3R,4S,5S)-4-acetamido-5-amino-3-((3S)-3-((2-(ethoxylcarbonyl)amino)ethoxyl)piperidin)-1-cyclohexene-1-carboxylate was prepared with reference to Example 1 b).

The characterization analysis of the product: ESI-MS m/z: 441.2 (M+H)$^+$.

c) Preparation of ethyl (3R,4S,5S)-4-acetamido-5-((tert-butyloxycarbonyl) amino)-3-((3S)-3-((2-(ethoxylcarbonyl)amino)ethoxyl)piperidin)-1-cyclohexene-1-carboxylate.

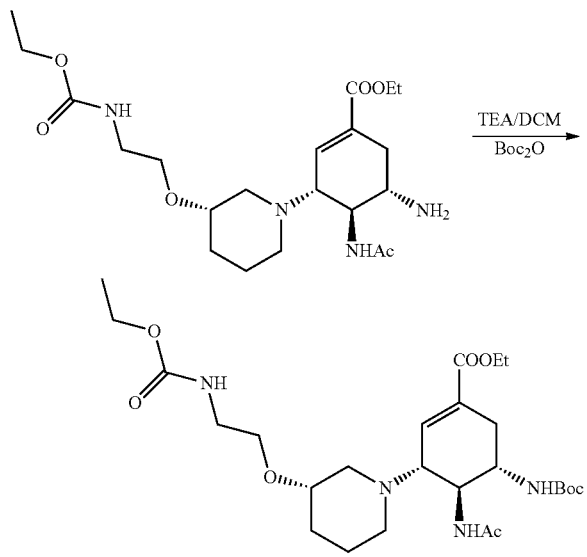

Ethyl (3R,4S,5S)-4-acetamido-5-((tert-butyloxycarbonyl)amino)-3-((3S)-3-((2-(ethoxylcarbonyl)amino)ethoxyl)piperidin)-1-cyclohexene-1-carboxylate was prepared with reference to Example 1 c).

The characterization analysis of the product: ESI-MS m/z: 541.2 (M+H)$^+$.

d) Preparation of (3R,4S,5S)-4-acetamido-5-((tert-butyloxycarbonyl) amino)-3-((3S)-3-((2-(ethoxylcarbonyl)amino)ethoxyl)piperidin)-1-cyclohexene-1-carboxylic acid.

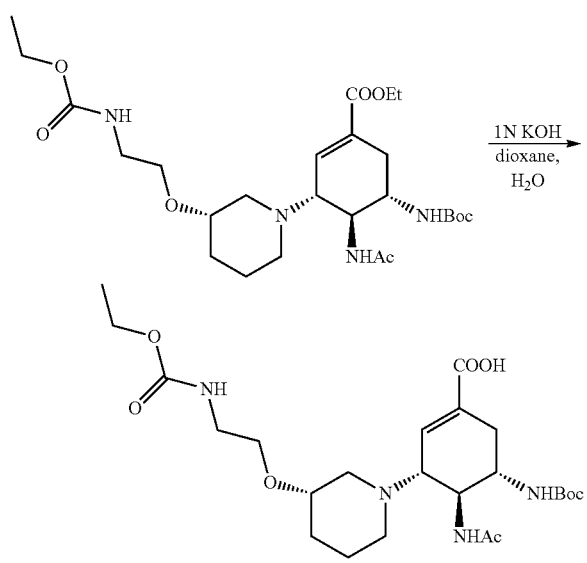

(3R,4S,5S)-4-acetamido-5-((tert-butyloxycarbonyl)amino)-3-((3S)-3-((2-(ethoxylcarbonyl)amino)ethoxyl)piperidin)-1-cyclohexene-1-carboxylic acid was prepared with reference to Example 1 d).

The characterization analysis of the product:
$^1$H-NMR(400 MHz,CDCl$_3$):δppm6.942(dd,1H,2-CH),5.456(m,1H,4-CH), 5.356(dd,1H,5-CH),4.145-4.008(m,2H,NHCOOCH$_2$CH$_3$),3.795-3.785(m,1H,3-CH),3.770-3.712(m,2H,OCH$_2$CH$_2$NH),3.486-3.398(m,2H,OCH$_2$CH$_2$NH),2.936-2.908(m,1H,NCH$_2$CH),2.791-2.700(m,2H,NCH$_2$CH$_2$,NCH$_2$CH),2.487-2.467(m,1H,NCH$_2$CH$_2$),2.351-2.331(m,1H,NCH$_2$CH),2.241-2.204(m,1H,6-CH$_2$),2.175-2.168(m,1H,6-CH$_2$),1.962(s,3H,COCH$_3$),1.627-1.578(m,1H,NCH$_2$CH$_2$CH$_2$),1.564-1.536(m,2H,NCH$_2$CH$_2$CH$_2$),1.521-1.489(m,1H,NCH$_2$CH$_2$CH$_2$),1.422(s,9H,C(CH$_3$)$_3$),1.255-1.202(m,3H,NHCOOCH$_2$CH$_3$).
ESI-MS m/z: 513.2 (M+H)$^+$.

e) Preparation of (3R,4S,5S)-4-acetamido-5-amino-3-((3S)-3-((2-(ethoxylcarbonyl)amino)ethoxyl)piperidin)-1-cyclohexene-1-carboxylic acid trifluoroacetate.

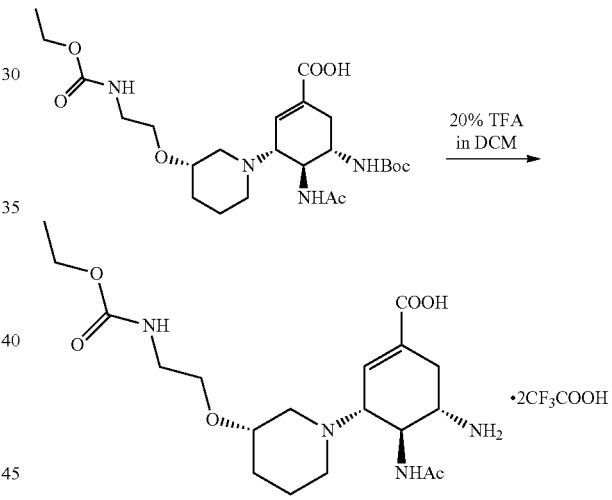

(3R,4S,5S)-4-acetamido-5-amino-3-((3S)-3-((2-(ethoxylcarbonyl)amino)ethoxyl)piperidin)-1-cyclohexene-1-carboxylic acid trifluoroacetate was prepared with reference to Example 1 e).

The characterization analysis of the product:
$^1$H-NMR(400 MHz,MeOD):δppm6.934(dd,1H,2-CH),4.360(m,1H,4-CH), 4.104-4.052(m,2H,NHCOOCH$_2$CH$_3$),3.805-3.789(m,1H,3-CH),3.783-3.756(m,2H,OCH$_2$CH$_2$NH),3.558-3.550(dd,1H,5-CH),3.496-3.389(m,2H$_2$OCH$_2$CH$_2$NH),2.969-2.926(m,1H,NCH$_2$CH),2.805-2.756(m,2H,NCH$_2$CH$_2$,NCH$_2$CH),2.528-2.501(m,1H,NCH$_2$CH$_2$),2.412-2.385(m,1H,NCH$_2$CH),2.352-2.220(m,1H,6-CH$_2$),2.196-2.163(m,1H,6-CH$_2$),1.984(s,3H,COCH$_3$),1.638-1.572(m,1H,NCH$_2$CH$_2$CH$_2$),1.561-1.535(m,2H,NCH$_2$CH$_2$CH$_2$),1.502-1.476(m,1H,NCH$_2$CH$_2$CH$_2$), 1.309-1.264(m,3H,NHCOOCH$_2$CH$_3$).
ESI-MS m/z: 413.2 (M+H)$^+$.

EXAMPLE 8 a) Preparation of ethyl (3R,4S,5S)-4-acetamido-5-azido-3-((3S)-3-(n-butoxymethyl)piperidin)-1-cyclohexene-1-carboxylate.

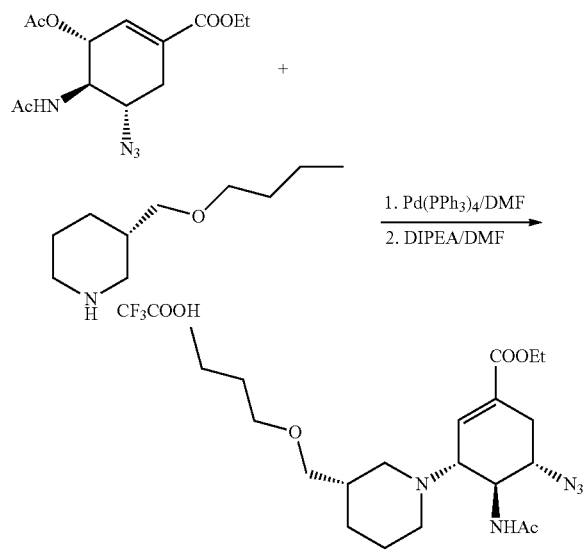

Ethyl (3R,4S,5S)-4-acetamido-5-azido-3-((3S)-3-(n-butoxymethyl) piperidin)-1-cyclohexene-1-carboxylate was prepared with reference to Example 1 a).

The characterization analysis of the product: ESI-MS m/z: 422.3 (M+H)$^+$.

b) Preparation of ethyl (3R,4S,5S)-4-acetamido-5-amino-3-((3S)-3-(n-butoxymethyl)piperidin)-1-cyclohexene-1-carboxylate.

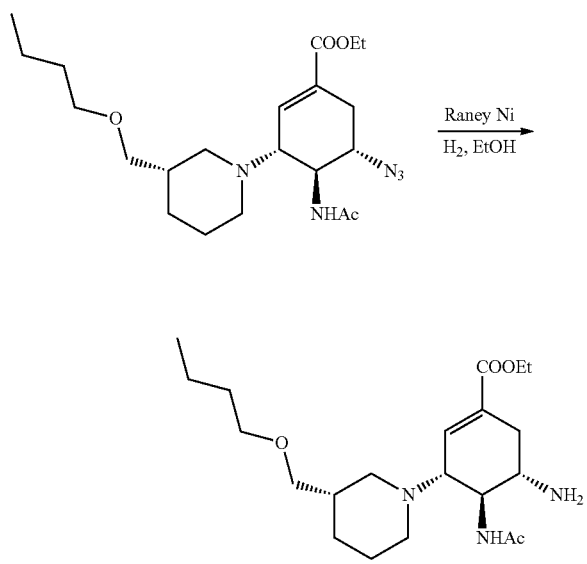

Ethyl (3R,4S,5S)-4-acetamido-5-amino-3-((3S)-3-(n-butoxymethyl) piperidin)-1-cyclohexene-1-carboxylate was prepared with reference to Example 1 b). The characterization analysis of the product: ESI-MS m/z: 396.2 (M+H)$^+$.

c) Preparation of ethyl (3R,4S,5S)-4-acetamido-5-((tert-butyloxycarbonyl) amino)-3-((3S)-3-(n-butoxymethyl) piperidin)-1-cyclohexene-1-carboxylate.

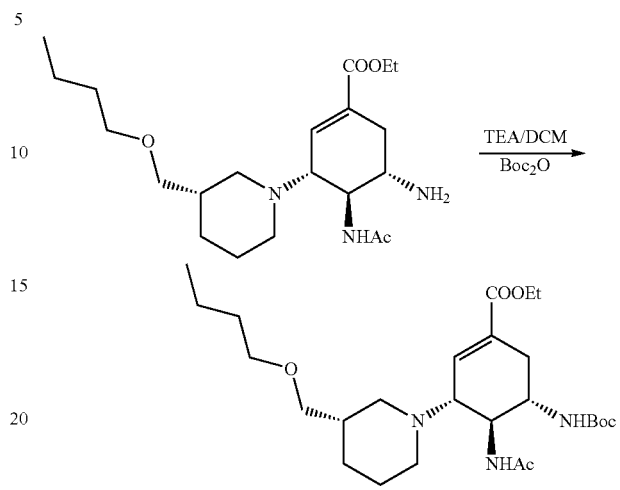

Ethyl (3R,4S,5S)-4-acetamido-5-((tert-butyloxycarbonyl) amino)-3-((3S)-3-(n-butoxymethyl)piperidin)-1-cyclohexene-1-carboxylate was prepared with reference to Example 1 c). The characterization analysis of the product: ESI-MS m/z: 496.2 (M+H)$^+$.

d) Preparation of (3R,4S,5S)-4-acetamido-5-((tert-butyloxycarbonyl) amino)-3-((3S)-3-(n-butoxymethyl) piperidin)-1-cyclohexene-1-carboxylic acid.

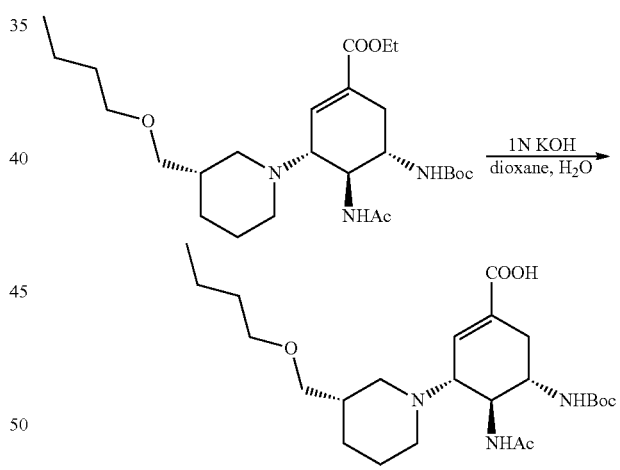

(3R,4S,5S)-4-acetamido-5-((tert-butyloxycarbonyl) amino)-3-((3S)-3-(n-butoxymethyl)piperidin)-1-cyclohexene-1-carboxylic acid was prepared with reference to Example 1 d).

The characterization analysis of the product:
$^1$H-NMR(400 MHz,CDCl$_3$):δppm6.869(dd,1H,2-CH),5.297(dd,1H,4-CH), 4.144-4.120(dd, 1H,5-CH),3.758-3.739(dd,1H,3-CH),3.689-3.612(m,1H,CHCH$_2$OCH$_2$),3.412-3.346(q,2H, OCH$_2$CH$_2$),3.329-3.286(m,1H,CHCH$_2$OCH$_2$),2.958-2.912(m,2H,NCH$_2$CH$_2$),2.495-2.483(m,1H,NCH$_2$CH),2.401-2.389(m,1H,6-CH$_2$),2.251-2.203(m,1H,NCH$_2$CH),2.044-2.035(m,1H,6-CH$_2$),1.988(s,3H,COC H̲₃),1.856-1.803(m,1H,NCH₂CH̲),1.717-1.681(m,3H,NCH₂CH₂CH̲₂,CH̲₂CH₂CH₃),1.568-1.501(m,3H,NCH₂CH̲₂CH₂,CH̲₂CH₂CH₃),1.422(s,9H,C(CH̲₃)₃),1.379-3.286(m,2H,CH₂CH̲₂CH₃),0.928-0.816(t,3H,CH₂CH₂CH̲₃).

ESI-MS m/z: 468.2 (M+H)⁺.

e) Preparation of (3R,4S,5S)-4-acetamido-5-amino-3-((3S)-3-(n-butoxymethyl) piperidin)-1-cyclohexene-1-carboxylic acid trifluoroacetate.

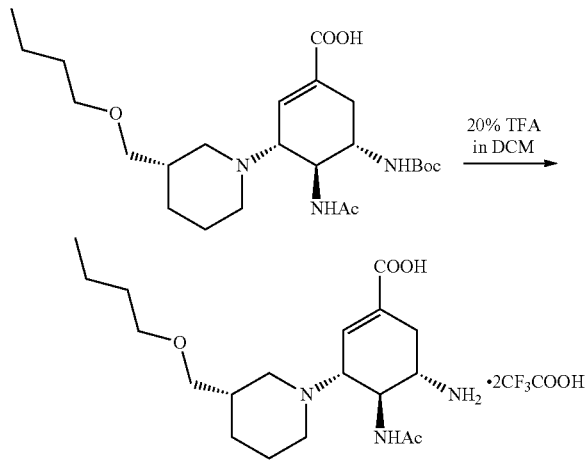

(3R,4S,5S)-4-acetamido-5-amino-3-((3S)-3-(n-butoxymethyl) piperidin)-1-cyclohexene-1-carboxylic acid trifluoroacetate was prepared with reference to Example 1 e).

The characterization analysis of the product:

¹-H-NMR(400 MHz,D₂O):δppm 6.962(dd,1H,2-CH̲),4.555-4.401(dd,1H,4-CH̲), 4.235-4.225(dd,1H,3-CH̲),3.601-3.515(m,1H,CHCH̲₂OCH₂),3.498-3.490(dd,1H,5-CH̲),3.458-3.401(q,2H,OCH̲₂CH₂),3.368-3.312(m,1H,CHCH̲₂OCH₂),2.986-2.916(m,2H,NCH̲₂CH),2.504-2.479(m,1H,NCH̲₂CH),2.434-2.392(m,1H,6-CH̲₂),2.286-2.249(m,1H,NCH̲₂CH),2.105-2.089(m,1H,6-CH̲₂),1.962(s,3H,COCH̲₃),1.871-1.825(m,1H,NCH₂CH̲),1.735-1.699(m,3H,NCH₂CH₂CH̲₂,CH̲₂CH₂CH₃),1.584-1.499(m,3H,NCH̲₂CH₂CH₂,CH̲₂CH₂CH₃), 1.385-3.274(m,2H,CH₂CH̲₂CH₃),0.999-0.826(t,3H,CH₂CH₂CH̲₃).

ESI-MS m/z: 368.2 (M+H)⁺.

EXAMPLE 9 a) Preparation of ethyl (3R,4S,5S)-4-acetamido-5-azido-3-((3S)-3-(2-((dimethylcarbamoyl) oxy)ethyoxyl)piperidin)-1-cyclohexene-1-carboxylate.

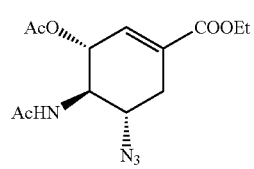

+

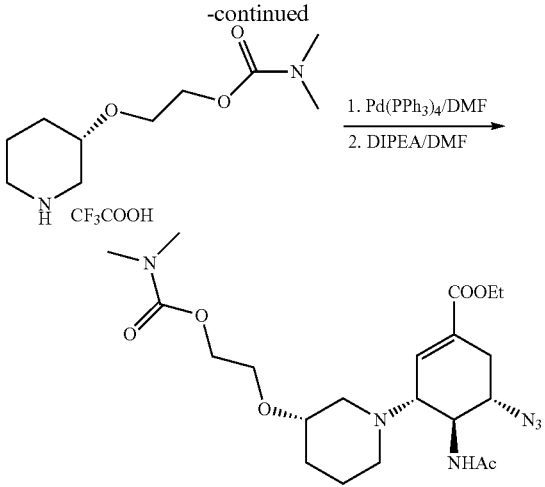

Ethyl (3R,4S,5S)-4-acetamido-5-azido-3-((3S)-3-(2-((dimethylcarbamoyl)oxy)ethyoxyl)piperidin)-1-cyclohexene-1-carboxylate was prepared with reference to Example 1 a).

The characterization analysis of the product:

¹H-NMR(400 MHz,CDCl₃):δppm6.857(s,1H,NH̲),5.577-5.555(dd,1H,2-CH̲), 4.662-4.617(m,1H,4-CH̲),4.286-4.179(m,2H,COOCH̲₂CH₃),4.059-3.869(m,2H,CH̲₂OCON),3.706-3.638(m,1H,3-CH̲),3.529-3.485(m,2H,OCH̲₂CH₂OCO),2.912-2.887(s,6H,N(CH̲₃)₂),2.826-2.816(m,2H,NCH₂CH̲, NCH̲₂CH₂CH₂),2.724-2.696(m,1H,NCH̲₂CH),2.593-2.546(m,1H,NCH̲₂CH₂CH₂),2.327-2.230(m,2H,NCH̲₂CH,5-CH̲),2.046-2.015(s,3H,COCH̲₃),1.952-1.913(m,1H,6-CH̲₂),1.712-1.653(m,2H,6-CH̲₂,NCH₂CH₂CH̲₂),1.512-1.409(m,2H,NCH̲₂CH₂CH₂),1.386-1.355(m,1H,NCH₂CH̲₂CH₂),1.346-1.298(t,3H,COOCH₂CH̲₃).

ESI-MS m/z: 467.3 (M+H)⁺.

Preparation of ethyl (3R,4S,5S) -4-acetamido-5-amino-3-((3S)-3-(2-((dimethylcarbamoyl)oxy)ethyoxyl)piperidin)-1-cyclohexene-1-carboxylate.

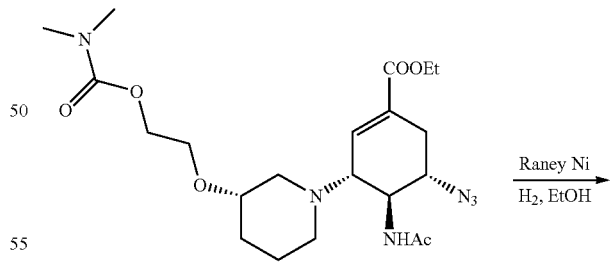

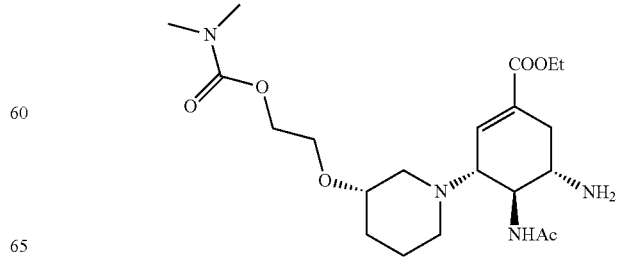

Ethyl (3R,4S,5S)-4-acetamido-5-amino-3-((3S)-3-(2-((dimethylcarbamoyl)oxy)ethyoxyl)piperidin)-1-cyclohexene-1-carboxylate was prepared with reference to Example 1 b).

The characterization analysis of the product: ESI-MS m/z: 441.2 (M+H)⁺.

c) Preparation of ethyl (3R,4S,5S)-4-acetamido-5-((tert-butyloxycarbonyl) amino)-3-((3S)-3-(2-((dimethylcarbamoyl) oxy)ethyoxyl)piperidin)-1-cyclohexene-1-carboxylate.

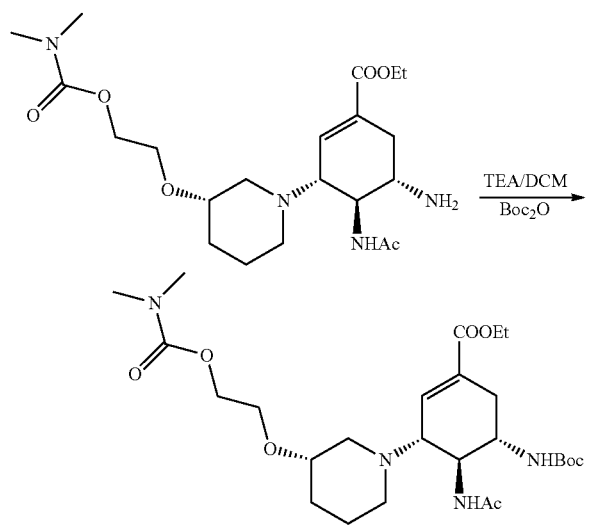

Ethyl (3R,4S,5S)-4-acetamido-5-((tert-butyloxycarbonyl) amino)-3-((3S)-3-(2-((dimethylcarbamoyl)oxy)ethyoxyl)piperidin)-1-cyclohexene-1-carboxylate was prepared with reference to Example 1 c). The characterization analysis of the product: ESI-MS m/z: 541.2 (M+H)⁺.

d) Preparation of (3R,4S,5S)-4-acetamido-5-((tert-butyloxycarbonyl) amino)-3-((3S)-3-(2-((dimethylcarbamoyl) oxy)ethyoxyl)piperidin)-1-cyclohexene-1-carboxylic acid.

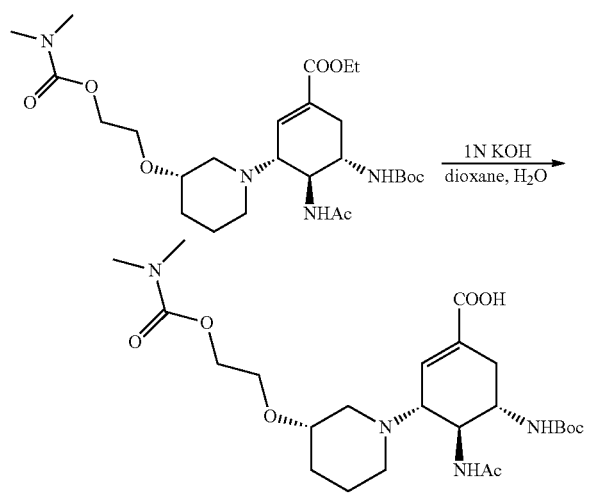

(3R,4S,5S)-4-acetamido-5-((tert-butyloxycarbonyl) amino)-3-((3S)-3-(2-((dimethylcarbamoyl)oxy)ethyoxyl)piperidin)-1-cyclohexene-1-carboxylic acid was prepared with reference to Example 1 d).

The characterization analysis of the product:
¹-H-NMR(400 MHz,MeOD):δppm6.824(m,1H,2-CH),4.840-4.586(m,1H,4-CH), 4.008-3.956(m,1H,5-CH),3.683-3.593(m,2H,CH₂OCON),3.495-3.472(m,1H,3-CH),2.946-2.898(s,6H,N(CH₃)₂),2.890-2.857(m,2H,OCH₂CH₂OCO),2.807-2.780(m,1H,NCH₂CH),2.728-2.717(m,1H,NCH₂CH),2.685-2.673(m,1H,NCH₂CH₂CH₂),2.630-2.584(m,1H,NCH₂CH₂CH₂),2.434-3.390(m,1H,NCH₂CH),2.214-2.144(m,2H,6-CH₂),1.989(s,3H,COCH₃),1.957-1.986(m,2H,NCH₂CH₂CH₂),1.740-1.722(m,1H,NCH₂CH₂CH₂),1.434(s,9H,C(CH₃)₃).
ESI-MS m/z: 513.3 (M+H)⁺.

e) Preparation of (3R,4S,5S)-4-acetamido-5-amino-3-((3S)-3-(2-((dimethylcarbamoyl)oxy)ethyoxyl)piperidin)-1-cyclohexene-1-carboxylic acid trifluoroacetate.

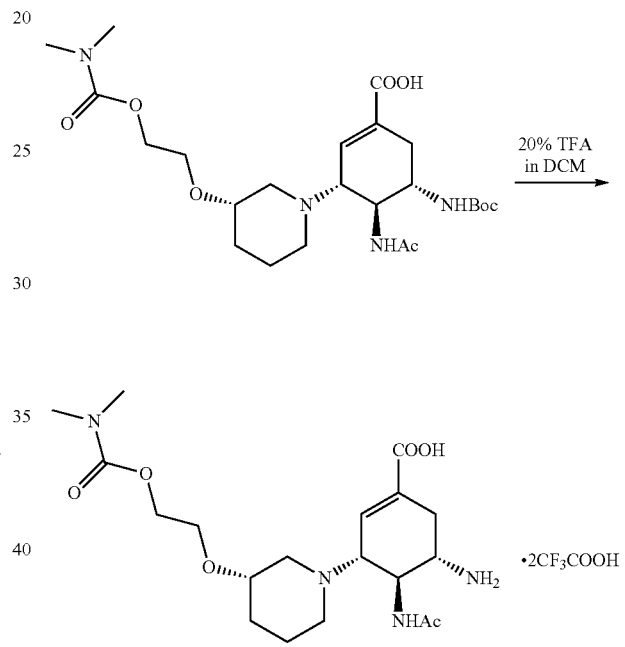

(3R,4S,5S)-4-acetamido-5-amino-3-((3S)-3-(2-((dimethylcarbamoyl)oxy)ethyoxyl)piperidin)-1-cyclohexene-1-carboxylic acid was prepared with reference to Example 1 e).

The characterization analysis of the product:
¹H-NMR(400 MHz,MeOD):δppm7.001(m,1H,2-CH),4.560-4.555(m,1H,4-CH), 4.291-4.268(m,2H,CH₂OCON),3.639-3.603(m,1H,3-CH),3.565-3.508(m,2H,OCH₂CH₂OCO),3.337-3.333(s,6H,N(CH₃)₂),3.289-3.275(m,1H,5-CH),3.106-3.007(m,1H,NCH₂CH),2.956-2.863(m,1H,NCH₂CH),2.731-2.699(m,1H,NCH₂CH₂CH₂),2.654-2.487(m,1H,NCH₂CH₂CH₂),2.455-2.346(m,1H,NCH₂CH),2.289-2.607(m,2H,6-CH₂),2.058(s,3HCOCH₃),1.969-1.946(m,2H,NCH₂CH₂CH₂),1.768-1.652(m,1H,NCH₂CH₂CH₂).
ESI-MS m/z: 413.3 (M+H)⁺.

EXAMPLE 10 a) Preparation of ethyl (3R,4S,5S)-4-acetamido-5-azido-3-((3S)-3-(2-((morpholine-4-carbonyl)oxy) ethyoxyl)piperidin)-1-cyclohexene-1-carboxylate.

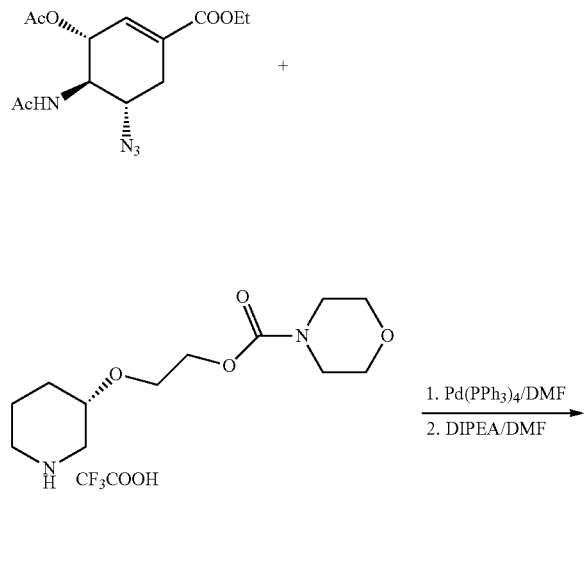

Ethyl (3R,4S,5S)-4-acetamido-5-azido-3-((3S)-3-(2-((morpholine-4-carbonyl)oxy)ethyoxyl)piperidin)-1-cyclohexene-1-carboxylate was prepared with reference to Example 1 a).

The characterization analysis of the product:

$^1$H-NMR(400 MHz,CDCl$_3$):δppm6.844(s,1H,NH),5.471-5.449(dd,1H,2-CH), 4.710-4.654(m,1H,4-CH),4.258-4.171(q,2H,COOCH$_2$CH$_3$),4.036-3.962(m,2H,CH$_2$OCON),3.692-3.664(m,4H,2xNCH$_2$CH$_2$O),3.456-3.433(m,6H,2xNCH$_2$CH$_2$O,OCH$_2$CH$_2$O),2.899-2.883(m,1H,NCH$_2$CH),2.880-2.873(m,2H,NCH$_2$CH,NCH$_2$CH$_2$CH$_2$),2.730-2.703(m,1H,NCH$_2$CH$_2$CH$_2$),2.594-2.546(m,1H,NCH$_2$CH),2.324-2.296(m,1H,5-CH),2.272-2.229(m,1H,6-CH$_2$),2.047(s,3H,COCH$_3$),1.993-1.938(m,1H,6-CH$_2$),1.697-1.643(m,2H, NCH$_2$CH$_2$CH$_2$),1.492-1.421(m,2H, NCH$_2$CH$_2$CH$_2$),1.392-1.304(t,3H, COOCH$_2$CH$_3$).

ESI-MS m/z: 509.3 (M+H)$^+$.

b) Preparation of ethyl (3R,4S,5S) -4-acetamido-5-amino-3-((3S)-3-(2-((morpholine-4-carbonyl)oxy)ethyoxyl)piperidin)-1-cyclohexene-1-carboxylate.

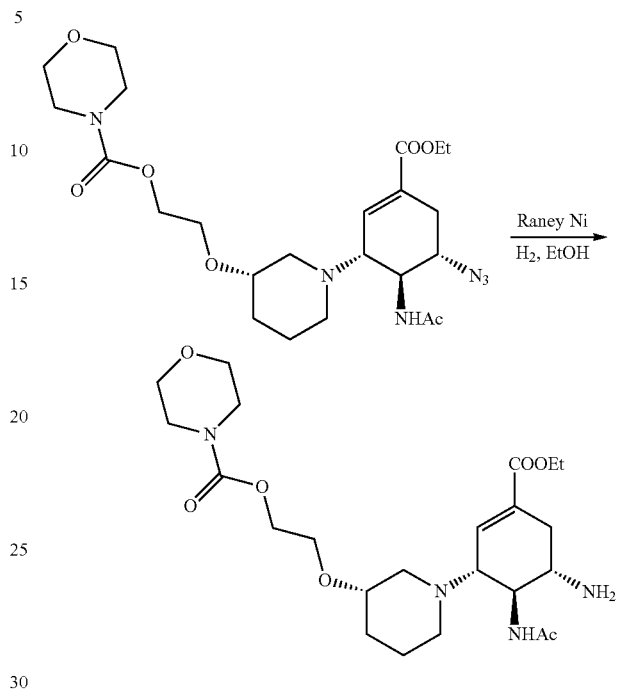

Ethyl (3R,4S,5S)-4-acetamido-5-amino-3-((3S)-3-(2-((morpholine-4-carbonyl)oxy)ethyoxyl)piperidin)-1-cyclohexene-1-carboxylate was prepared with reference to Example 1 b). The characterization analysis of the product: ESI-MS m/z: 483.2 (M+H)$^+$.

c) Preparation of ethyl (3R,4S,5S)-4-acetamido-5-((tert-butyloxycarbonyl) amino)-3-((3S)-3-(2-((morpholine-4-carbonyl)oxy)ethyoxyl)piperidin)-1-cyclohexene-1-carboxylate.

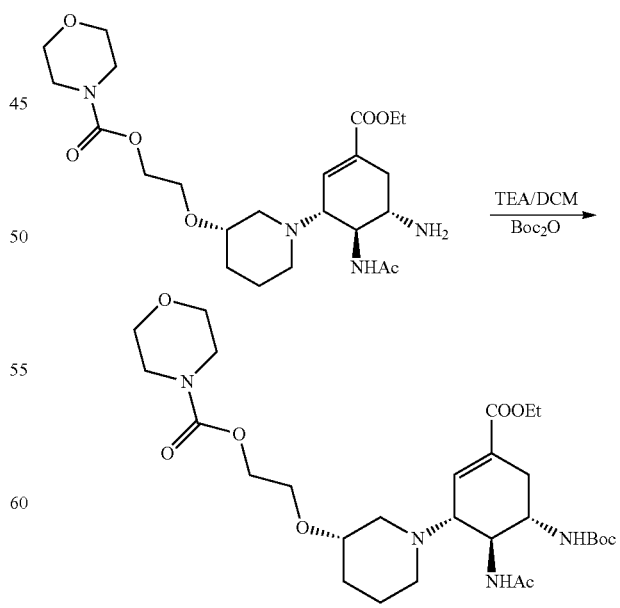

Ethyl (3R,4S,5S)-4-acetamido-5-((tert-butyloxycarbonyl) amino)-3-((3S)-3-(2-((morpholine-4-carbonyl)oxy)

ethyoxyl)piperidin)-1-cyclohexene-1-carboxylate was prepared with reference to Example 1 c). The characterization analysis of the product: ESI-MS m/z: 583.3 (M+H)⁺.

d) Preparation of (3R,4S,5S)-4-acetamido-5-((tert-butyloxycarbonyl) amino)-3-((3S)-3-(2-((morpholine-4-carbonyl)oxy)ethyoxyl)piperidin)-1-cyclohexene-1-carboxylic acid.

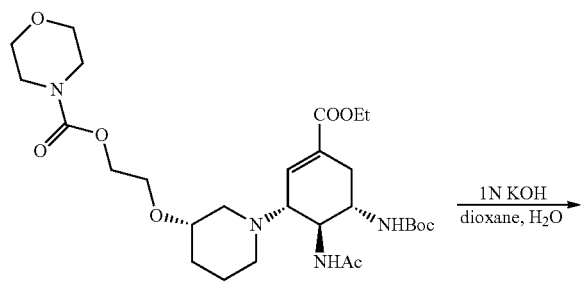

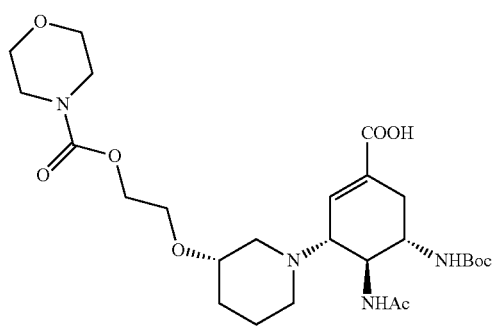

(3R,4S,5S)-4-acetamido-5-((tert-butyloxycarbonyl) amino)-3-((3S)-3-(2-((morpholine-4-carbonyl)oxy) ethyoxyl)piperidin)-1-cyclohexene-1-carboxylic acid was prepared with reference to Example 1 d).

The characterization analysis of the product: ESI-MS m/z: 555.2 (M+H)⁺.

e) Preparation of (3R,4S,5S)-4-acetamido-5-amino-3-((3S)-3-(2-((morpholine-4-carbonyl)oxy)ethyoxyl)piperidin)-1-cyclohexene-1-carboxylic acid trifluoroacetate.

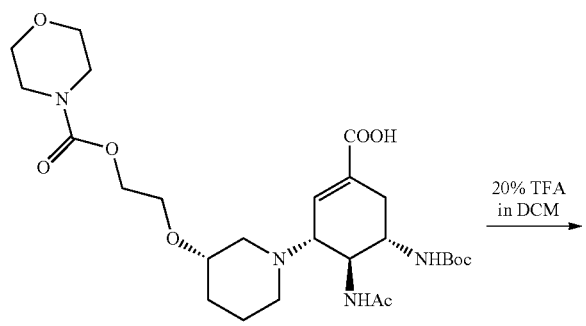

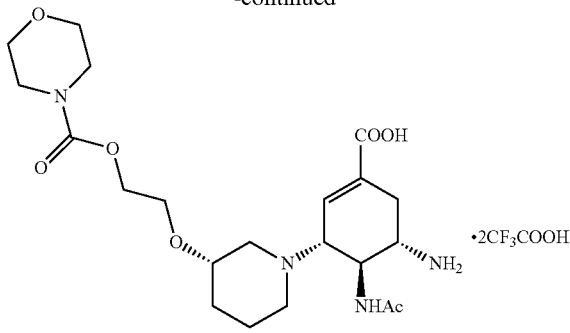

(3R,4S,5S)-4-acetamido-5-amino-3-((3S)-3-(2-((morpholine-4-carbonyl)oxy) ethyoxyl)piperidin)-1-cyclohexene-1-carboxylic acid trifluoroacetate was prepared with reference to Example 1 e).

The characterization analysis of the product:
¹H-NMR(400 MHz,MeOD):δppm6.993(dd,1H,2-C$\underline{H}$),4.335-4.286(m,2H, C$\underline{H}_2$OCON), 4.245-4.223(m,1H,4-C$\underline{H}$),3.914-3.897(m,1H,5-C$\underline{H}$),3.663-3.604(m,4H, 2xNC$\underline{H}_2$CH$_2$O),3.856-3.450(m,6H,2xNCH$_2$C$\underline{H}_2$O,OC$\underline{H}_2$CH$_2$O),3.102-3.054(m,1H,NCH$_2$C$\underline{H}$),3.002-2.921(m,2H,NC$\underline{H}_2$CH,NC$\underline{H}_2$CH$_2$CH$_2$),2.912-2.886(m,1H,NC$\underline{H}_2$CH$_2$CH$_2$),2.765-2.744(m,1H,NC$\underline{H}_2$CH),2.736-2.720(m,1H,6-C$\underline{H}_2$),2.512-2.443(m,1H,6-C$\underline{H}_2$),2.085(s,3H,COC$\underline{H}_3$),1.947-1.927(m,2H, NCH$_2$CH$_2$C$\underline{H}_2$),1.664-1.652(m,2H, NCH$_2$C$\underline{H}_2$CH$_2$).
ESI-MS m/z: 455.2 (M+H)⁺.

EXAMPLE 11 a) Preparation of ethyl(3R,4R,5S)-4-acetamido-5-(2,3-bis(tert-butoxycarbonyl)guanidino)-3-((3S)-3-(2-methoxyl-ethyoxyl)piperidin)-1-cyclohexene-1-carboxylate.

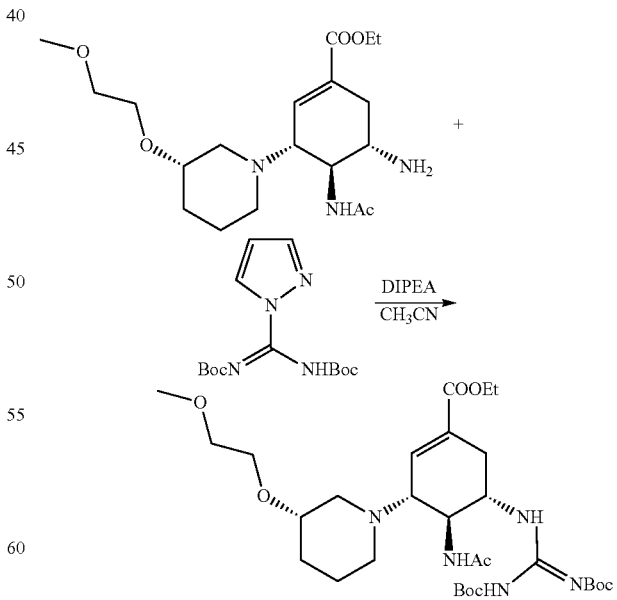

According to the above equation, 0.5 mmol of ethyl(3R,4R,5S)-4-acetamido-5-amino-3-((3S)-3-(2-methoxyl-ethyoxyl)piperidin)-1-cyclohexene-1-carboxylate was added into a single neck flask, and 10 mL of acetonitrile was added and stirred at room temperature. Then 1.55 mmol of DIPEA and 0.5 mmol of N, N'-bis-BOC-1H-1-guanidinopyrazole was added, and the mixture was kept stirring at room temperature for 3 hours. Once TLC (PE:EA=1:1) indicated the reaction was completed, 20 ml of water was added, and the mixture was extracted with EA, dried with anhydrous sodium sulfate and evaporated to dryness. After being purified by the column (PE:EA=3:1), a white solid was obtained.

The characterization analysis of the product:
$^1$H-NMR(400 MHz,CDCl$_3$):δppm6.909(s,1H,NHAc),6.273-6.253(m,1H,2-CH), 4.345-4.286(m,1H,4-CH),4.211-4.198(q,2H,COOCH$_2$CH$_3$),4.188-4.111(m,1H,3-CH),3.659-3.570(m,2H,OCH$_2$CH$_2$OCH$_3$),3.525-3.503(m,2H,OCH$_2$CH$_2$OCH$_3$),3.378(s,3H,OCH$_2$CH$_2$OCH$_3$),3.327-3.315(m,1H,5-CH),2.918-2.866(m,1H,NCH$_2$CH),2.824-2.800(m,2H,NCH$_2$CH,NCH$_2$CH$_2$CH$_2$),2.525-2.476(m,1H,NCH$_2$CH$_2$CH$_2$),2.315-2.283(m,1H,NCH$_2$CH),2.179-2.126(m,1H,6-CH),2.041-2.022(m,1H,6-CH),1.998(s,3H,COCH$_3$),1.991-1.661(m,3H,NCH$_2$CH$_2$CH$_2$),1.493(s,18H,2xC(CH$_3$)$_3$),1.432-1.425(m,1H,NCH$_2$CH$_2$),1.312-1.286(t,3H,COOCH$_2$CH$_3$).

ESI-MS m/z: 626.43 (M+H)+.

b) Preparation of ethyl (3R,4R,5S)-4-acetamido-5-(2,3-bis(tert-butoxycarbonyl)guanidino)-3-((3S)-3-(2-methoxylethyoxyl)piperidin)-1-cyclohexene-1-carboxylic acid.

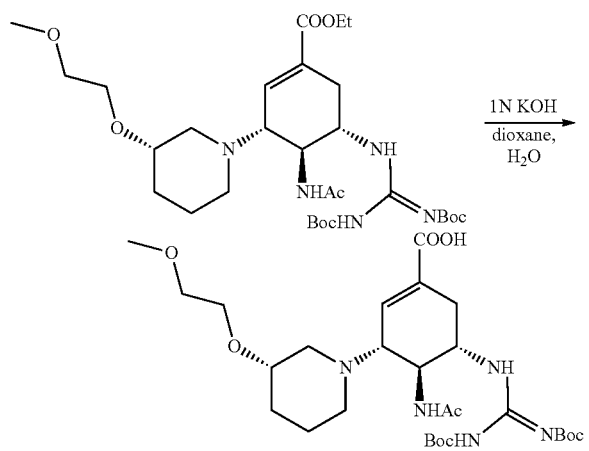

0.368 mmol of ethyl (3R,4R,5S)-4-acetamido-5-(2,3-bis(tert-butoxycarbonyl)guanidino)-3-((3S)-3-(2-methoxylethyoxyl)piperidin)-1-cyclohexene-1-carboxylate was added into a single neck flask, and 5.5 ml of 1,4-dioxane, 0.55 mol of water, and 0.55 ml of 1N KOH aqueous solution were then added and stirred overnight at room temperature. Once TLC (PE:EA=1:1) indicated the reaction was completed, the solvent was evaporated to dryness through an oil pump, 5 ml of methanol was then added for dissolution. Acid resin was used for adjusting pH to 5, the mixture was filtered, evaporated to dryness, and eluted by column purification (DCM:MeOH=10:1). A white solid was obtained finally.

The characterization analysis of the product:
$^1$H-NMR(400 MHz,CDCl$_3$):δppm6.949(s,1H,NHAc),4.323-4.304(m,1H,2-CH), 4.188-4.167(m,1H,4-CH),3.635-3.628(m,1H,3-CH),3.622-3.585(m,2H,OCH$_2$CH$_2$OCH$_3$),3.528-3.518(m,2H,OCH$_2$CH$_2$OCH$_3$),3.489-3.465(m,1H,5-CH),3.561-3.440(m,1H,NCH$_2$CH),3.388-3.372(s,3H,OCH$_2$CH$_2$OCH$_3$),3.016-2.908(m,1H,NCH$_2$CH),2.878-2.864(m,1H,NCH$_2$CH$_2$CH$_2$),2.557-2.525(m,1H,NCH$_2$CH$_2$CH$_2$),2.324-2.294(m,1H,NCH$_2$CH),2.286-2.224(m,1H,6-CH),1.993-1.956(m,1H,6-CH),1.924(s,3H,COCH$_3$),1.716-1.695(m,1H,NCH$_2$CH$_2$CH$_2$),1.612-1.535(m,2H,NCH$_2$CH$_2$CH$_2$),1.484(s,18H,2xC(CH$_3$)$_3$),1.321-1.255(m,1H, NCH$_2$CH$_2$CH$_2$).

ESI-MS m/z: 598.3 (M+H)+$^+$.

c) Preparation of (3R,4R,5S)-4-acetamido-5-guanidino-3-((3S)-(2-methoxylethyoxyl)piperidin)-1-cyclohexene-1-carboxylic acid trifluoroacetate.

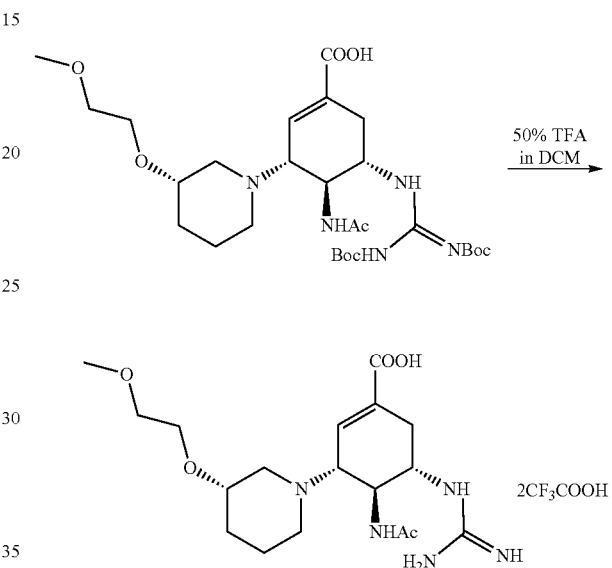

(3R,4S,5S)-4-acetamido-5-5-(2,3-bis(tert-butoxycarbonyl)guanidino)-3-((3S)-3-(2-methoxylethyoxyl)piperidin)-1-cyclohexene-1-carboxylic acid was added into a single neck flask, and the solution of 50% DCM in TFA was then added and stirred at room temperature for 1 hour. Once TLC (DCM:MeOH=10:1) indicated the reaction was completed, the solvent was evaporated to dryness and the excess TFA was drawn out through an oil pump. Diethyl ether was added for trituration. After filtering, a white solid product was obtained.

The characterization analysis of the product:
$^1$H-NMR(400 MHz,MeOD):δppm6.973(m,1H,2-CH),4.385-4.368(m,1H,4-CH), 3.947-3.934(m,1H,3-CH),3.922-3.906(m,1H,5-CH),3.724-3.653(m,2H,OCH$_2$CH$_2$OCH$_3$),3.633-3.626(m,1H,NCH$_2$CH),3.597-3.588(m,2H$_2$OCH$_2$CH$_2$OCH$_3$),3.512-3.478(m,1H,NCH$_2$CH),3.414(s,3H,OCH$_2$CH$_2$OCH$_3$),3.161-3.131(m,1H,NCH$_2$CH$_2$CH$_2$),3.034-3.021(m,1H,NCH$_2$CH$_2$CH$_2$),2.898-2.877(m,1H,NCH$_2$CH),2.479-2.407(m,1H,6-CH),2.289-2.156(m,1H,6-CH),2.074(s,3H,COCH$_3$),1.988-1.876(m,2H,NCH$_2$CH$_2$CH$_2$),1.828-1.793(m,2H,NCH$_2$CH$_2$CH$_2$).

ESI-MS m/z for the product: 398.3 (M+H)$^+$.

EXAMPLE 12 a) Preparation of ethyl(3R,4R,5S)-4-acetamido-5-(2,3-bis(tert-butoxycarbonyl)guanidino)-3-((3R)-3-(2-methoxylethyoxyl)piperidin)-1-cyclohexene-1-carboxylate.

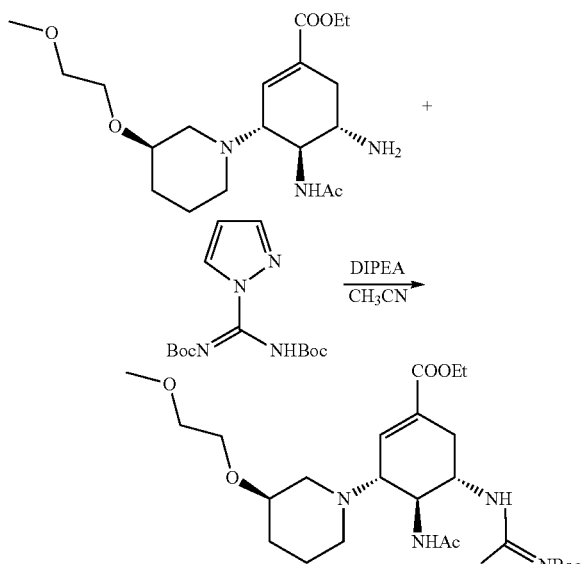

Ethyl(3R,4R,5S)-4-acetamido-5-(2,3-bis (tert-butoxycarbonyl)guanidino)-3-((3R)-3-(2-methoxylethyoxyl)piperidin)-1-cyclohexene-1-carboxylate was prepared according to Example 11 a).

The characterization analysis of the product:
$^1$H-NMR(400 MHz,CDCl$_3$):δppm6.98(s,1H,NHAc),6.278-6.263(m,1H,2-CH), 4.356-4.292(m,1H,4-CH),4.219-4.204(q,2H,COOCH$_2$CH$_3$),4.195-4.125(m,1H,3-CH),3.670-3.589(m,2H,OCH$_2$CH$_2$OCH$_3$),3.560-3.521(m,2H,OCH$_2$CH$_2$OCH$_3$),3.381(s,3H,OCH$_2$CH$_2$OCH$_3$),3.337-3.322(m,1H,5-CH),2.915-2.862(m,1H,NCH$_2$CH),2.828-2.805(m,2H,NCH$_2$CH,NCH$_2$CH$_2$CH$_2$),2.558-2.492(m,1H,NCH$_2$CH$_2$),2.321-2.292(m,1H,NCH$_2$CH),2.186-2.122(m,1H, 6-CH),2.098-2.057(m,1H,6-CH),1.997(s,3H,COCH$_3$),1.990-1.668(m,3H,NCH$_2$CH$_2$),1.495(s,18H,2xC(CH$_3$)$_3$),1.435-1.427(m,1H,NCH$_2$CH$_2$CH$_2$),1.315-1.283(t,3H,COOCH$_2$CH3).

ESI-MS m/z: 626.4 (M+H)$^+$.

b) Preparation of (3R,4R,5S)-4-acetamido-5-(2,3-bis(tert-butoxycarbonyl)guanidino)-3-((3R)-3-(2-methoxylethyoxyl)piperidin)-1-cyclohexene-1-carboxylic acid.

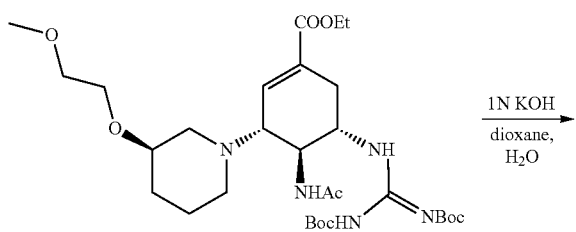

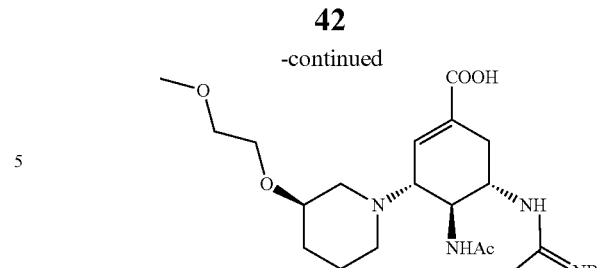

(3R,4R,5S)-4-acetamido-5-(2,3-bis(tert-butoxycarbonyl)guanidino)-3-((3R)-3-(2-methoxylethyoxyl)piperidin)-1-cyclohexene-1-carboxylic acid was prepared according to Example 11 b).

The characterization analysis of the product:
$^1$H-NMR(400 MHz,CDCl$_3$):δppm6.963(s,1H,NHAc),4.353-4.311(m,1H,2-CH), 4.193-4.172(m,1H,4-CH),3.641-3.635(m,1H,3-CH),3.635-3.588(m,2H,OCH$_2$CH$_2$OCH$_3$),3.535-3.522(m,2H,OCH$_2$CH$_2$OCH$_3$),3.492-3.469(m, 1H,5-CH),3.573-3.450(m,1H,NCH$_2$CH),3.394-3.379(s,3H,OCH$_2$CH$_2$OCH$_3$),3.030-2.928(m,1H,NCH$_2$CH),2.890-2.869(m,1H,NCH$_2$CH$_2$CH$_2$),2.562-2.532(m,1H,NCH$_2$CH$_2$CH$_2$),2.330-2.290(m,1H,NCH$_2$CH),2.286-2.222(m,1H,6-CH),1.998-1.967(m,1H,6-CH),1.929(s,3H,COCH$_3$),1.720-1.698(m,1H,NCH$_2$CH$_2$CH$_2$),1.623-1.530(m,2H,NCH$_2$CH$_2$CH$_2$),1.491(s,18H,2xC(CH$_3$)$_3$),1.322-1.261(m,1H, NCH$_2$CH$_2$CH$_2$).

ESI-MS m/z: 598.3 (M+H)$^+$.

c) Preparation of (3R,4R,5S)-4-acetamido-5-guanidino-3-((3R)-3-(2-methoxylethyoxyl)piperidin)-1-cyclohexene-1-carboxylic acid trifluoroacetate.

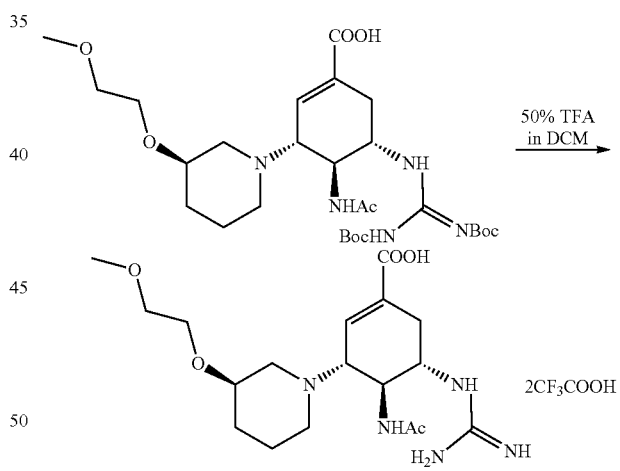

(3R,4R,5S)-4-acetamido-5-guanidino-3-((3R)-3-(2-methoxylethyoxyl) piperidin)-1-cyclohexene-1-carboxylic acid trifluoroacetate was prepared with reference to the Example 11 c).

The characterization analysis of the product:
$^1$H-NMR(400 MHz,MeOD):δppm6.978(m,1H,2-CH),4.389-4.372(m,1H,4-CH),3.952-3.938(m,1H,3-CH),3.929-3.903(m,1H,5-CH),3.732-3.661(m,2H,OCH$_2$CH$_2$OCH$_3$),3.635-3.629(m,1H,NCH$_2$CH),3.601-3.591(m,2H,OCH$_2$CH$_2$OCH$_3$),3.519-3.476(m,1H,NCH$_2$CH),3.421(s,3H,OCH$_2$CH$_2$OCH$_3$),3.169-3.129(m,1H,NCH$_2$CH$_2$CH$_2$),3.089-3.065(m,1H,NC H₂CH₂CH₂),2.901-2.898(m,1H,NCH₂CH),2.482-2.411(m,1H,6-CH₂CH),2.296-2.165(m,1H,6-CH),2.095(s,3H,COCH₃),1.991-1.867(m,2H,NCH₂CH₂CH₂),1.835-1.798(m,2H,NCH₂CH₂CH₂).

ESI-MS m/z for the product: 398.3 (M+H)⁺.

EXAMPLE 13 a) Preparation of ethyl(3R,4S,5S)-4-acetamido-5-azido-3-((3R)-3-((2-(methoxylethyoxyl)methyl)piperidin)-1-cyclohexene-1-carboxylate.

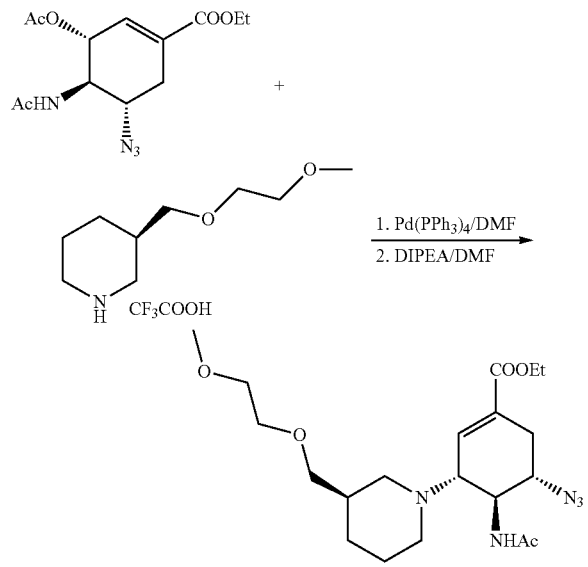

Ethyl(3R,4S,5S)-4-acetamido-5-azido-3-((3R)-3-((2-(methoxylethyoxyl)methyl)piperidin)-1-cyclohexene-1-carboxylate was prepared with reference to Example 1 a).

The characterization analysis of the product: ESI-MS m/z: 424.2 (M+H)⁺.

b) Preparation of ethyl (3R,4S,5S)-4-acetamido-5-amino-3-((3R)-3-((2-(methoxylethyoxyl)methyl)piperidin)-1-cyclohexene-1-carboxylate.

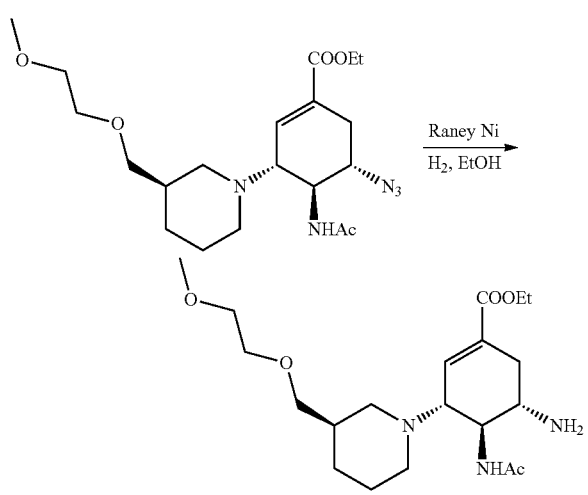

Ethyl (3R,4S,5S)-4-acetamido-5-amino-3-((3R)-3-((2-(methoxylethyoxyl)methyl)piperidin)-1-cyclohexene-1-carboxylate was prepared with reference to Example 1 b).

The characterization analysis of the product: ESI-MS m/z: 398.2 (M+H)⁺.

c) Preparation of ethyl(3R,4R,5S)-4-acetamido-5-(2,3-bis((tert-butyloxycarbonyl)guanidine)-3-((3R)-3-((2-(methoxylethyoxyl)methyl)piperidin)-1-cyclohexene-1-carboxylate.

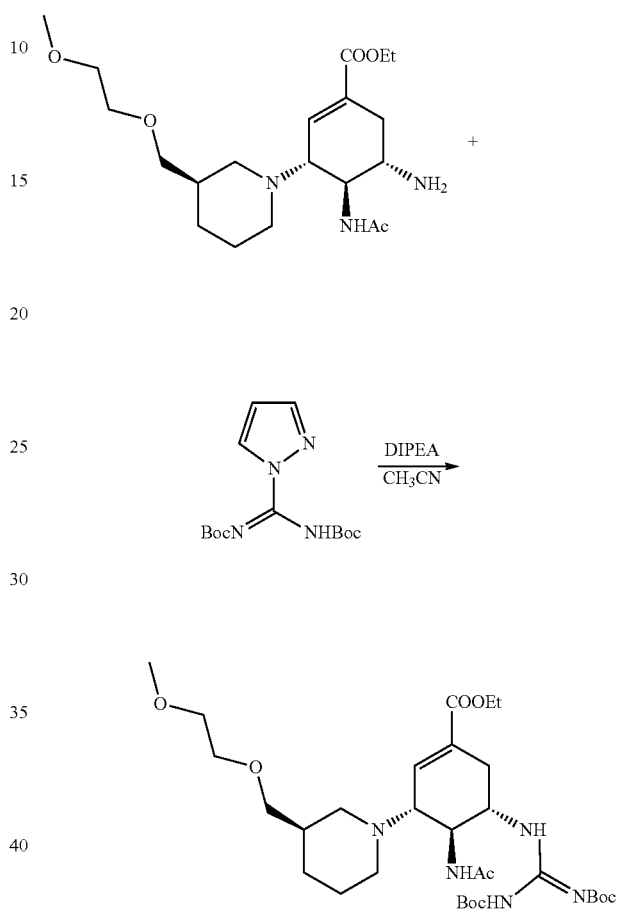

Ethyl(3R,4R,5S)-4-acetamido-5-(2,3-bis((tert-butyloxycarbonyl)guanidine)-3-((3R)-3-((2-(methoxylethyoxyl)methyl)piperidin)-1-cyclohexene-1-carboxylate was prepared with reference to Example 11 a).

The characterization analysis of the product:
¹H-NMR(400 MHz,CDCl₃):δppm6.668-6.563(m,1H,2-CH),4.352-4.298(m,1H,4-CH),4.235-4.216(q,2H,COOCH2CH3),4.198-4.130(m,1H,3-CH),3.670-3.589(m,2H,OCH2CH2OCH3),3.560-3.535(m,4H,OCH2CH2OCH3),3.391-3.388(m,2H,CHCH2OCH2CH2OCH3)3.382-3.379(m,1H,5-CH),3.369(s,3H,OCH2CH2OCH3),2.925-2.860(m,1H,NCH2CH),2.836-2.809(m,2H,NCH2CH,NCH2CH2CH2),2.569-2.498(m,1H,NCH2CH2CH2),2.335-2.296(m,1H,NCH2CH),2.190-2.120(m,1H,6-CH),2.101-2.086(m,1H,6-CH),1.999(s,3H,COCH3),1.989-1.670(m,3H,NCH2CH2CH2),1.497(s,18H,2xC(CH3)3),1.447-1.435(m,1H,NCH2CH2CH2),1.339-1.291(t,3H,COOCH2CH3).

ESI-MS m/z: 640.4 (M+H)⁺.

d) Preparation of (3R,4R,5S)-4-acetamido-5-(2,3-bis(tert-butoxycarbonyl)guanidino)-3-((3R)-3-((2-(methoxylethyoxyl)methyl)piperidin)-1-cyclohexene-1-carboxylic acid.

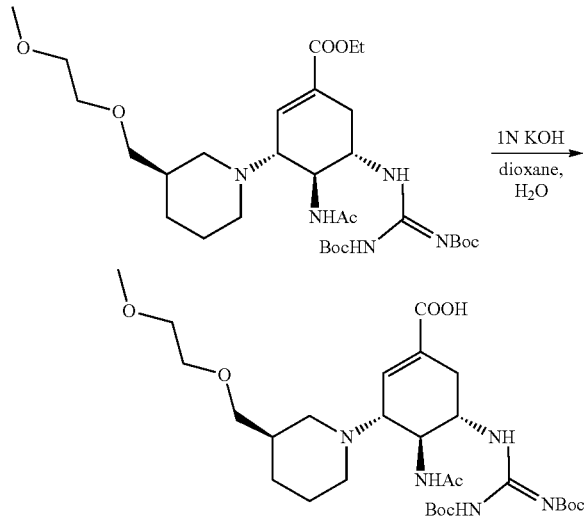

(3R,4R,5S)-4-acetamido-5-(2,3-bis(tert-butoxycarbonyl)guanidino)-3-((3R)-3-((2-(methoxylethyoxyl)methyl)piperidin)-1-cyclohexene-1-carboxylic acid was prepared with reference to the Example 11 b).

The characterization analysis of the product:
$^1$H-NMR(400 MHz,CDCl$_3$):δppm6.670-6.559(m,1H,2-C$\underline{H}$),4.363-4.302(m,1H,4-C$\underline{H}$),4.205-4.139(m,1H,3-C$\underline{H}$),3.678-3.592(m,2H,OCH$_2$C$\underline{H}_2$OCH$_3$),3.589-3.539(m,4H,OC$\underline{H}_2$C$\underline{H}_2$OCH$_3$),3.396-3.389(m,2H,CHC$\underline{H}_2$OCH$_2$CH$_2$OCH$_3$),3.389-3.382(m,1H,5-C$\underline{H}$)3.380(s,3H,OCH$_2$CH$_2$OC$\underline{H}_3$),2.929-2.875 (m,1H,NCH$_2$C$\underline{H}$),2.826-2.803(m,2H,NC$\underline{H}_2$CH,NC$\underline{H}_2$CH$_2$CH$_2$),2.573-2.506(m,1H,NC$\underline{H}_2$CH$_2$CH$_2$),2.345-2.306(m,1H,NC$\underline{H}_2$CH),2.198-2.133(m,1H,6-C$\underline{H}$),2.109-2.098(m,1H,6-C$\underline{H}$),1.997(s,3H,COC$\underline{H}_3$),1.990-1.686(m,3H,NCH$_2$C$\underline{H}_2$C$\underline{H}_2$),1.495(s,18H,2xC(C$\underline{H}_3$)$_3$),1.452-1.430(m,1H,NCH$_2$C$\underline{H}_2$CH$_2$).

ESI-MS m/z: 612.4 (M+H)$^+$.

e) Preparation of (3R,4R,5S)-4-acetamido-5-guanidino-3-((3R)-3-((2-(methoxylethyoxyl)methyl)piperidin)-1-cyclohexene-1-carboxylic acid trifluoroacetate.

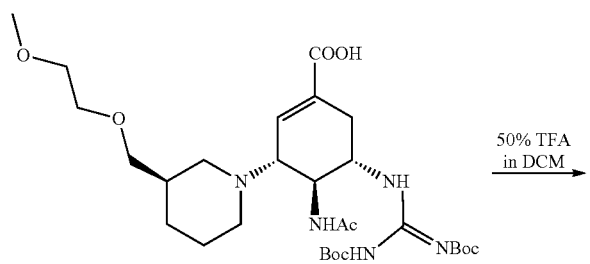

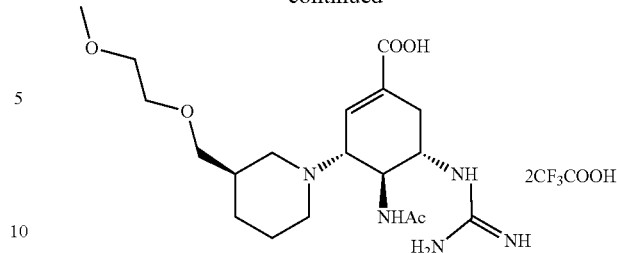

(3R,4R,5S)-4-acetamido-5-guanidino-3-((3R)-3-((2-(methoxylethyoxyl)methyl)piperidin)-1-cyclohexene-1-carboxylic acid trifluoroacetate was prepared with reference to the Example 11 c).

The characterization analysis of the product:
$^1$H-NMR(400 MHz,MeOD):δppm6.675-6.555(m,1H,2-C$\underline{H}$),4.368-4.312(m,1H,4-C$\underline{H}$),4.265-4.239(m,1H,3-C$\underline{H}$),3.698-3.605(m,2H,OCH$_2$C$\underline{H}_2$OCH$_3$),3.589-3.545(m,4H,OC$\underline{H}_2$C$\underline{H}_2$OCH$_3$),3.405-3.395(m,2H,CHC$\underline{H}_2$OCH$_2$CH$_2$OCH$_3$),3.390-3.380(m,1H,5-C$\underline{H}$)3.379(s,3H,OCH$_2$CH$_2$OC$\underline{H}_3$),2.935-2.881(m,1H,NCH$_2$C$\underline{H}$),2.833-2.809(m,2H,NC$\underline{H}_2$CH,NC$\underline{H}_2$CH$_2$CH$_2$),2.586-2.526(m,1H,NC$\underline{H}_2$CH$_2$CH$_2$),2.352-2.316(m,1H,NC$\underline{H}_2$CH),2.201-2.140(m,1H,6-C$\underline{H}$),2.120-2.105 (m,1H,6-C$\underline{H}$),1.998(s,3H,COC$\underline{H}_3$),1.991-1.696(m,3H,NCH$_2$C$\underline{H}_2$C$\underline{H}_2$),1.465-1.445(m,1H,NCH$_2$C$\underline{H}_2$CH$_2$).

ESI-MS m/z: 412.4 (M+H)$^+$.

EXAMPLE 14 a) Preparation of ethyl(3R,4R,5S)-4-acetamido-5-(2,3-bis(tert-butoxycarbonyl)guanidino)-3-((3S)-3-(2-ethyoxylmethyl)piperidin)-1-cyclohexene-1-carboxylate.

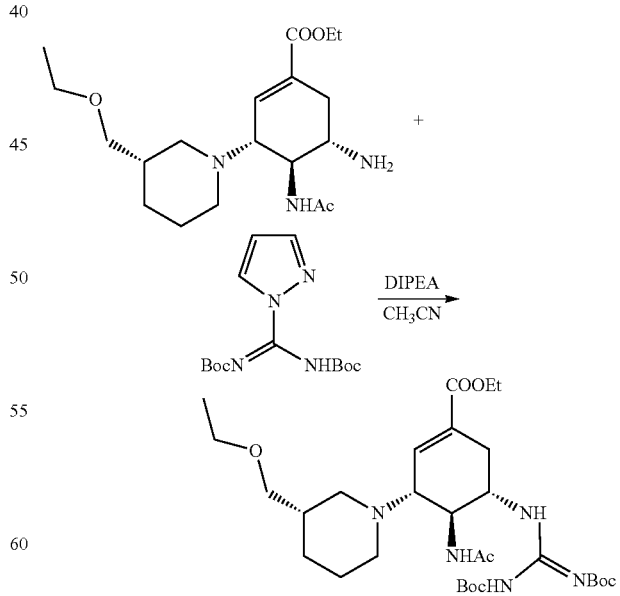

Ethyl(3R,4R,5S)-4-acetamido-5-(2,3-bis(tert-butoxycarbonyl)guanidino)-3-((3S)-3-(2-ethyoxylmethyl)piperidin)-1-cyclohexene-1-carboxylate was prepared with reference to Example 11 a).

The characterization analysis of the product:

$^1$H-NMR(400 MHz,CDCl$_3$):δppm6.979(s,1H,NHAc),6.384-6.365(m,1H,2-CH),4.421-4.409(m,1H,4-CH),4.223-4.205(q,2H,COOCH$_2$CH$_3$),4.005-3.988(q,2H,CH$_2$OCH$_2$CH$_3$),3.821-3.756(m,1H,3-CH),3.512-3.489(m,1H,5-CH),3.435-3.371(m,1H,CH$_2$OCH$_2$CH$_3$),3.338-3.246(m,1H,CH$_2$OCH$_2$CH$_3$),2.612-2.548(m,1H,NCH$_2$CH$_2$),2.453-2.439(m,1H,NCH$_2$CH$_2$),2.357-2.291(m,2H,6-CH$_2$,NCH),2.152-2.073(m,2H,6-CH$_2$,NCH),1.988(s,3H,COCH$_3$),1.895-1.837(m,1H,NCH$_2$CH),1.612-1.586(m,1H,NCH$_2$CH$_2$CH$_2$),1.541-1.512(m,2H,NCH$_2$CH$_2$),1.505-1.496(m,1H,NCH$_2$CH$_2$CH$_2$),1.490(s,9H,C(CH$_3$)$_3$),1.485(s,9H,C(CH$_3$)$_3$),1.325-1.295(t,3H,COOCH$_2$CH$_3$),1.121-1.109(t,3H,CH$_2$OCH$_2$CH$_3$).

ESI-MS m/z: 610.4 (M+H)$^+$.

b) Preparation of (3R,4R,5S)-4-acetamido-5-(2,3-bis(tert-butoxycarbonyl)guanidino)-3-((3S)-3-(2-ethyoxylmethyl)piperidin)-1-cyclohexene-1-carboxylic acid.

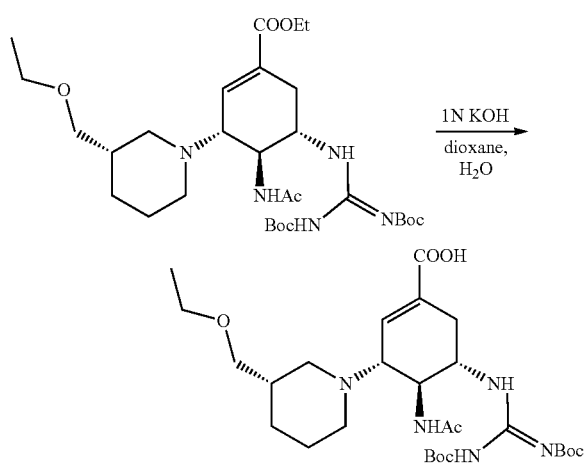

(3R,4R,5S)-4-acetamido-5-(2,3-bis(tert-butoxycarbonyl)guanidino)-3-((3S)-3-(2-ethyoxylmethyl)piperidin)-1-cyclohexene-1-carboxylic acid was prepared with reference to Example 11 b).

The characterization analysis of the product:

$^1$-H-NMR(400 MHz,MeOD):δppm6.797(m,1H,2-CH),4.339-4.312(m,1H,4-CH),3.856-3.798(m,1H,3-CH),3.524-3.472(q,2H,CH$_2$OCH$_2$CH$_3$),3.418-3.395(m,1H,CH$_2$OCH$_2$CH$_3$),3.756-3.371(m,1H,5-CH),3.338-3.246(m,1H,CH$_2$OCH$_2$CH$_3$),3.179-3.154(m,1H,NCH$_2$CH$_2$),3.117-3.091(m,1H,NCH$_2$CH$_2$),2.987-2.947(m,1H,NCH),2.693-2.641(m,1H,6-CH$_2$),2.595-2.541(m,1H,NCH),2.362-2.304(m,1H,6-CH$_2$),2.056-2.005(m,1H,NCH$_2$CH),1.982(s,3H,COCH$_3$),1.828-1.741(m,2H,NCH$_2$CH$_2$),1.645-1.614(m,2H,NCH$_2$CH$_2$CH$_2$),1.555(s,9H,C(CH$_3$)$_3$),1.490(s,9H,C(CH$_3$)$_3$),1.214-1.156(t,3H,CH$_2$OCH$_2$CH$_3$).

ESI-MS m/z: 582.3 (M+H)+.

c) Preparation of (3R,4R,5S)-4-acetamido-5-guanidino-3-((3S)-3-(2-ethyoxylmethyl)piperidin)-1-cyclohexene-1-carboxylic acid trifluoroacetate.

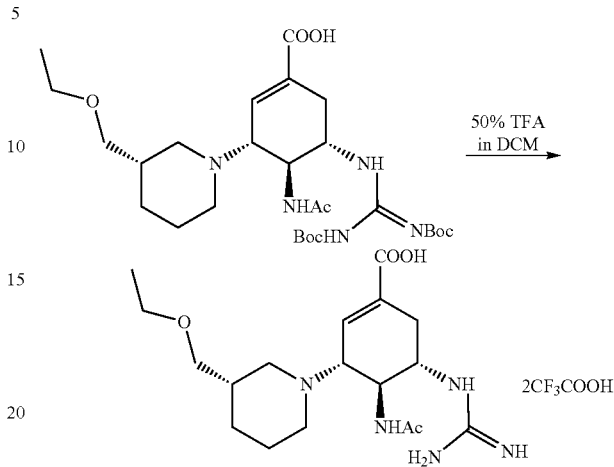

(3R,4R,5S)-4-acetamido-5-guanidino-3-((3S)-3-(2-ethyoxylmethyl)piperidin)-1-cyclohexene-1-carboxylic acid trifluoroacetate was prepared with reference to Example 11 c).

The characterization analysis of the product:

$^1$H-NMR(400 MHz,D$_2$O):δppm6.854(m,1H,2-CH),4.468-4.454(q,2H,CH$_2$OCH$_2$CH$_3$),3.949-3.938(m,1H,4-CH),3.639-3.604(m,1H,3-CH),3.582-3.564(q,2H,CH$_2$OCH$_2$CH$_3$),3.547-3.539(m,1H,CH$_2$OCH$_2$CH$_3$),3.529-3.518(m,1H,5-CH),3.514-3.507(m,1H,CH$_2$OCH$_2$CH$_3$)3.489-3.465(m,1H,NCH$_2$CH$_2$),3.425-3.404(m,1H,NCH$_2$CH$_2$),3.382-3.371(m,1H,NCH),3.120-3.151(m,1H,6-CH$_2$),2.970-2.926(m,1H,NCH),2.521-2.496(m,1H,6-CH$_2$),2.449-2.346(m,1H,NCH$_2$CH),2.081(s,3H,COCH$_3$),2.028-1.981(m,1H,NCH$_2$CH$_2$),1.885-1.779(m,2H,NCH$_2$CH$_2$),1.268-1.236(m,1H,NCH$_2$CH$_2$CH$_2$),1.195-1.161(t,3H,CH$_2$OCH$_2$CH$_3$).

ESI-MS m/z: 382.3 (M+H)$^+$.

Contrast Example 1

(3R,4R,5S)-4-acetamido-5-amino-3-((3S)-3-(2-ethyoxylmethyl)piperidin)-1-cyclohexene-1-carboxylic acid trifluoroacetate was prepared with reference to the method used in above Example 1, and its structure was shown hereinafter.

The characterization analysis of the product:

$^1$H-NMR(400 MHz,D$_2$O):δppm6.970(dd,1H,2-CH),4.476-4.425(dd,1H,4-CH),4.325-4.267(dd,1H,5-CH),3.694-3.586(dd,1H,3-CH),3.597-3.471(m,4H,OCH$_2$CH$_3$,CHCH$_2$O),3.436-3.430(dd,1H,NCH$_2$),3.089-3.056(dd,1H,NCH$_2$),3.050-3.021(dd,1H,NCH),2.825-2.654(dd,1H,NCH),2.532-2.463(dd,1H,6-CH$_2$),2.086-2.195(dd,1H,6-CH$_2$),2.028(s,3H,COCH$_3$),1.983-1.948(m,1H,NCH$_2$CH),1.812-1.705(m,3H,NCH$_2$CH$_2$CH$_2$,NCH$_2$CH$_2$),1.313-1.299(m,1H,NCH$_2$CH$_2$),1.193-1.159(t,3H,OCH$_2$CH$_3$).

ESI-MS m/z: 340.2 (M+H)$^+$.

Contrast Example 2

(3R,4R,5S)-4-acetamido-5-amino-3-((3R)-3-(2-ethyoxyl-methyl)piperidin)-1-cyclohexene-1-carboxylic acid trifluoroacetate was prepared with reference to the method used in above Example 1, and its structure was shown hereinafter.

The characterization analysis of the product:
$^1$H-NMR(400 MHz,D$_2$O):δppm6.975(dd,1H,2-CH),4.482-4.463(dd,1H,4-CH), 4.352-4.278(dd,1H,5-CH),3.702-3.642(dd,1H,3-CH),3.609-3.495(m,4H,OCH$_2$CH$_3$,CHCH$_2$O),3.457-3.449(dd,1H,NCH$_2$CH$_2$),3.102-3.087(dd,1H,NCH$_2$CH$_2$),3.068-3.043(dd,1H,NCH$_2$CH),2.863-2.735(dd,1H,NCH$_2$CH),2.612-2.489(dd,1H,6-CH$_2$),2.108-2.095(dd,1H,6-CH$_2$),2.003(s,3H,COCH$_3$),1.987-1.965(m,1H,NCH$_2$CH),1.826-1.735(m,3H,NCH$_2$CH$_2$CH$_2$,NCH$_2$CH$_2$CH$_2$),1.356-1.312(m,1H,NCH$_2$CH$_2$),1.201-1.169(t,3H,OCH$_2$CH$_3$).

ESI-MS m/z: 340.2 (M+H)$^+$.

Contrast Example 3

(3R,4R,5S)-4-acetamido-5-amino-3-((3S)-3-((2,2,2-trifluoroethoxyl)methyl)piperidin)-1-cyclohexene-1-carboxylic acid trifluoroacetate was prepared with reference to the method used in above Example 1, and its structure was shown hereinafter.

The characterization analysis of the product:
$^1$H-NMR(400 MHz,D$_2$O):δppm6.975(dd,1H,2-CH),4.482-4.463(dd,1H,4-CH), 4.352-4.278(dd,1H,5-CH),3.702-3.642(dd,1H,3-CH),3.609-3.495(m,4H,OCH$_2$CH$_3$,CHCH$_2$O),3.457-3.449(dd,1H,NCH$_2$CH$_2$),3.102-3.087(dd,1H,NCH$_2$CH$_2$),3.068-3.043(dd,1H,NCH$_2$CH),2.863-2.735(dd,1H,NCH$_2$CH),2.612-2.489(dd,1H,6-CH$_2$),2.108-2.095(dd,1H,6-CH$_2$),2.003(s,3H,COCH$_3$),1.987-1.965(m,1H,NCH$_2$CH),1.826-1.735(m,3H,NCH$_2$CH$_2$CH$_2$,NCH$_2$CH$_2$CH$_2$),1.356-1.312(m,1H,NCH$_2$CH$_2$),1.201-1.169(t,3H,OCH$_2$CH$_3$).

ESI-MS m/z: 340.2 (M+H)$^+$.

Experimental Examples

Activity assay for influenza virus neuraminidase.
Experimental materials:
NA (neuraminidase) solution: allantoic fluid of chicken embryo infected by influenza virus;
Enzyme catalyzed reaction system:
330 mmol/L of MES buffer solution (pH 3.5);
200 μmol/L of fluorogenic substrate MUNANA (2'-(4-methylumbelliferyl)-α-D-N-acetylneuraminic acid);
4 mmol/L of CaCl$_2$ solution;
Stop buffer: 14 mmol/L of NaOH solution (14 mmol/L, 83% ethanol);
Oseltamivir: 1 mmol/L;
Enzyme activity assay:
NA solution (with different diluted concentration) 40 μl;
MES (fatty acid methyl ester sulfonate) (330 mmol/L): 10 μl;
CaCl$_2$ (4 mmol/L): 10 μl;
MUNANA (200 μmol/L): 10 μl;
H$_2$O: 30 μl;
The above materials were mixed together and incubated for 15 minutes, and 150 μl of the stop buffer was added: EX=355 nm XM=460 nm Note: The dynamic curve of fluorescence values can be detected without addition of the stop buffer, in order to verify whether the enzyme reaction system works normally.

Experiment operation for screening a NA inhibitor is as follows:

1. Oseltamivir or the compounds prepared in Examples 1-12 were diluted in proportion of 1:10, 1:100, 1:1000, 1:10000.

2. Reaction steps: 30 μl of NA solution and 10 μl of Oseltamivir, or the compounds prepared in Examples 1-12 were well mixed and incubated for 30 minutes, and following ingredients were then added: 10 μl of MES (330 mmol/L), 10 μl of CaCl$_2$(4 mmol/L), 10 μl of MUNANA (200 μl), and 30 μl of H$_2$O. After they were well mixed and incubated for 15 minutes, 150 μl of the stop buffer was added and well mixed finally. The fluorescence values were detected: EX=355 nm XM=460 nm.

3. Data analysis: analyzed by GraphPad Prism Demo, and the assay results are shown in the table below:

TABLE 1

Inhibiting activity for influenza virus neuraminidase

| EXAMPLE | COMPOUND STRUCTURE | WIDE-TYPE IC$_{50}$ (nM) | H274Y MUTANT DRUG-RESISTANT STRAIN IC$_{50}$ (nM) |
|---|---|---|---|
| 1 | 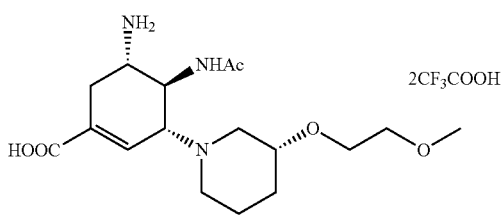 [SMILES: COCCO[C@@H]1CCCN([C@@H]2C=C(C(=O)O)C[C@H](N)[C@H]2NC(C)=O)C1] | a | a |

TABLE 1-continued

Inhibiting activity for influenza virus neuraminidase

| EXAMPLE | COMPOUND STRUCTURE | WIDE-TYPE IC$_{50}$ (nM) | H274Y MUTANT DRUG-RESISTANT STRAIN IC$_{50}$ (nM) |
|---|---|---|---|
| 2 | 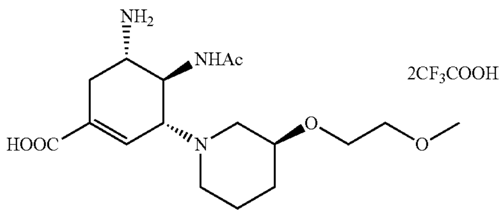 [SMILES: COCCO[C@H]1CCCN([C@@H]2C=C(C(=O)O)C[C@H](N)[C@H]2NC(C)=O)C1] | b | b |
| 3 | 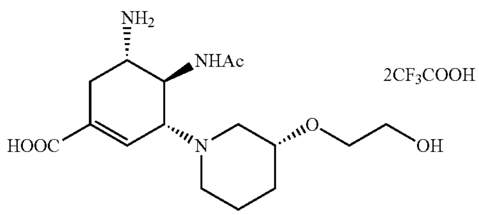 [SMILES: CC(=O)N[C@H]1[C@H](N2CCC[C@@H](OCCO)C2)C=C(C(=O)O)C[C@@H]1N] | b | b |
| 4 | 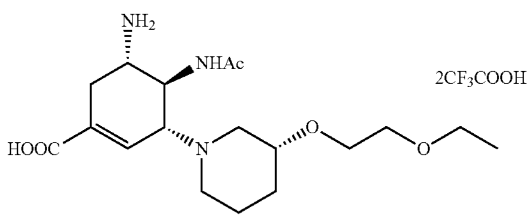 [SMILES: CCOCCO[C@@H]1CCCN([C@@H]2C=C(C(=O)O)C[C@H](N)[C@H]2NC(C)=O)C1] | b | b |
| 5 | 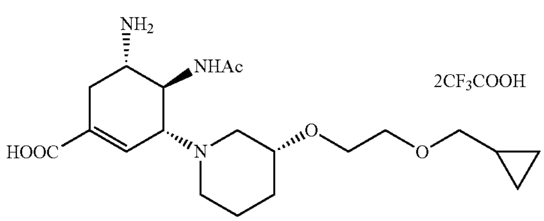 [SMILES: CC(=O)N[C@H]1[C@H](N2CCC[C@@H](OCCOCC3CC3)C2)C=C(C(=O)O)C[C@@H]1N] | a | b |
| 6 | 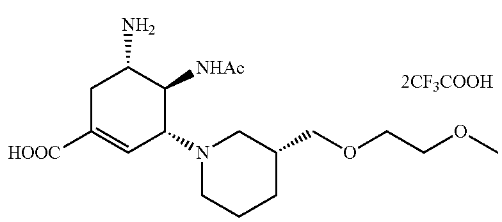 [SMILES: COCCOC[C@@H]1CCCN([C@@H]2C=C(C(=O)O)C[C@H](N)[C@H]2NC(C)=O)C1] | b | b |
| 7 | 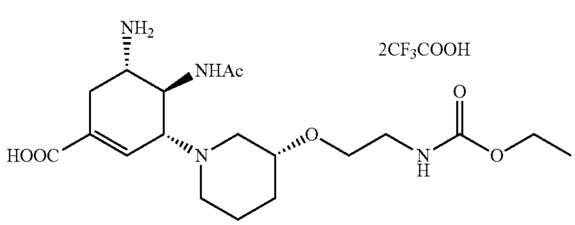 [SMILES: CCOC(=O)NCCO[C@@H]1CCCN([C@@H]2C=C(C(=O)O)C[C@H](N)[C@H]2NC(C)=O)C1] | b | b |

TABLE 1-continued
Inhibiting activity for influenza virus neuraminidase
| EXAMPLE | COMPOUND STRUCTURE | WIDE-TYPE IC$_{50}$ (nM) | H274Y MUTANT DRUG-RESISTANT STRAIN IC$_{50}$ (nM) |
|---------|--------------------|---------------------------|----------------------------------------------------|
| 8 | 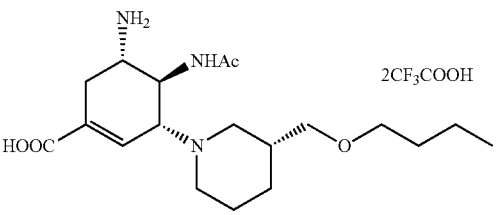 [SMILES: CCCCOC[C@@H]1CCCN([C@@H]2C=C(C(=O)O)C[C@H](N)[C@H]2NC(C)=O)C1] | b | b |
| 9 | 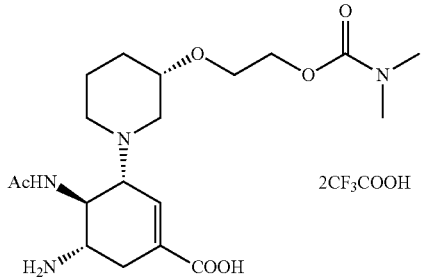 [SMILES: CC(=O)N[C@H]1[C@H](N2CCC[C@H](OCCOC(=O)N(C)C)C2)C=C(C(=O)O)C[C@@H]1N] | b | b |
| 10 | 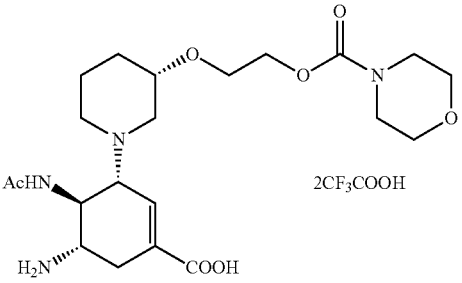 [SMILES: CC(=O)N[C@H]1[C@H](N2CCC[C@H](OCCOC(=O)N3CCOCC3)C2)C=C(C(=O)O)C[C@@H]1N] | c | b |
| 11 | 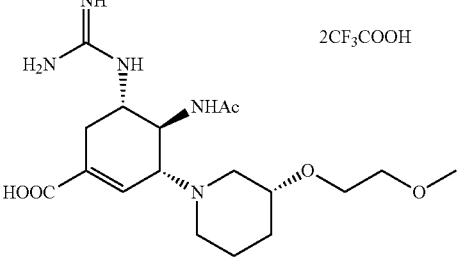 | a | a |
| 12 | 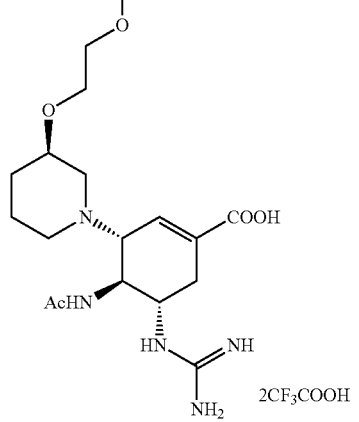 | b | b |

TABLE 1-continued

Inhibiting activity for influenza virus neuraminidase

| EXAMPLE | COMPOUND STRUCTURE | WIDE-TYPE $IC_{50}$ (nM) | H274Y MUTANT DRUG-RESISTANT STRAIN $IC_{50}$ (nM) |
|---|---|---|---|
| 13 | [structure with methoxyethoxymethyl piperidine, cyclohexene COOH, AcHN, guanidine, 2CF₃COOH] | b | b |
| 14 | [structure with guanidine, NHAc, HOOC cyclohexene, piperidine ethoxymethyl, 2CF₃COOH] | b | b |
| POSITIVE CONTROL | Oseltamivir phosphate | a | c |
| CONTRAST EXAMPLE 1 | [structure with NH₂, NHAc, HOOC cyclohexene, piperidine ethoxymethyl, 2CF₃COOH] | b | b |
| CONTRAST EXAMPLE 2 | [structure with NH₂, NHAc, HOOC cyclohexene, piperidine ethoxymethyl, 2CF₃COOH] | b | b |
| CONTRAST EXAMPLE 3 | [structure with NH₂, NHAc, HOOC cyclohexene, piperidine OCH₂CF₃, 2CF₃COOH] | b | b |

Note: a: <5 nM; b: 5 nM-100 nM; c: 100-1000 nM. nM is nmol/L.

It can be seen from the above results that the compounds disclosed in the present disclosure show great inhibiting activities on influenza viruses, and the activity will significantly increase when guanidine is located on $C_5$ site of the compound, or the substituent in S configuration is in the 3 site of piperidine ring. In addition, the compounds of all examples show great inhibiting activities on NA of H274Y mutant viruses strains which are drug-resistant to Oseltamivir. Specifically, Examples 1 and 11 further show a perfect inhibiting activities on wild-type and H274 mutant virus strains. This shows their application prospect in terms of preparation of anti-influenza drug, and a new drug is expected.

Although the present invention has been disclosed in the form of preferred embodiments and variations thereon, it will be understood that numerous additional modifications and variations could be made thereto without departing from the scope of the invention.

For the sake of clarity, it is to be understood that the use of 'a' or 'an' throughout this application does not exclude a plurality, and 'comprising' does not exclude other steps or elements.

The invention claimed is:

1. A cyclohexene compound having a structural formula II or a pharmaceutically acceptable salt, a stereoisomer thereof:

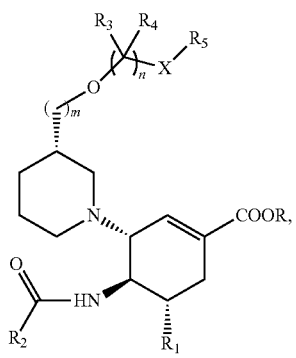

II wherein,
m is selected from 0 or 1;
R is selected from H;
$R_1$ is selected from amino, or guanidyl;
$R_2$ is selected from $C_1$-$C_4$ alkyl;
$R_3$ and $R_4$ are independently selected from H;
$R_5$ is absent, or $R_5$ is selected from H, $C_1$-$C_4$ alkyl, substituted $C_1$-$C_4$ alkyl, $C_3$-$C_6$ cycloalkyl, substituted $C_3$-$C_6$ cycloalkyl, $C_3$-$C_6$ heterocyclyl, or substituted $C_3$-$C_6$ heterocyclyl;
n is selected from 2;
X is selected from O, NHCOO, or OCONR$_9$R$_{10}$; and
$R_9$ and $R_{10}$ are independently selected from H, $C_1$-$C_4$ alkyl, substituted $C_1$-$C_4$ alkyl, $C_3$-$C_6$ cycloalkyl, or substituted $C_3$-$C_6$ cycloalkyl, or $R_9$ and $R_{10}$ together with the atom to which they are attached form a $C_3$-$C_6$ heterocyclic ring containing O and NH.

2. The cyclohexene compound or a pharmaceutically acceptable salt, or a stereoisomer thereof according to claim 1, wherein the cyclohexene compound is a compound having formula III:

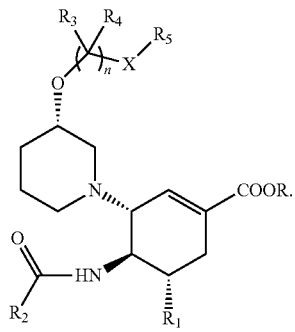

III

3. The cyclohexene compound or a pharmaceutically acceptable salt, or a stereoisomer thereof according to claim 1, wherein,
the substituted $C_1$-$C_4$ alkyl is selected from hydroxyethyl, methoxyethyl, ethoxyethyl, or cyclopropylmethyl; and
the substituted $C_3$-$C_6$ heterocyclyl is selected from morpholine-4-carbonyloxy4.

4. The cyclohexene compound or a pharmaceutically acceptable salt, or a stereoisomer thereof according to claim 1, wherein the cyclohexene compound is a compound selected from one of the following compounds:

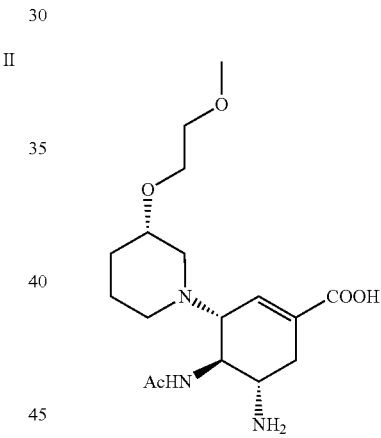

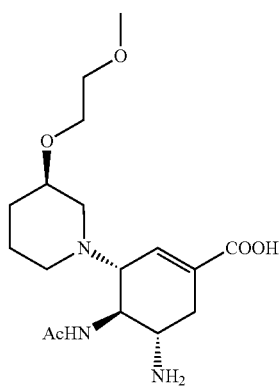

59
-continued
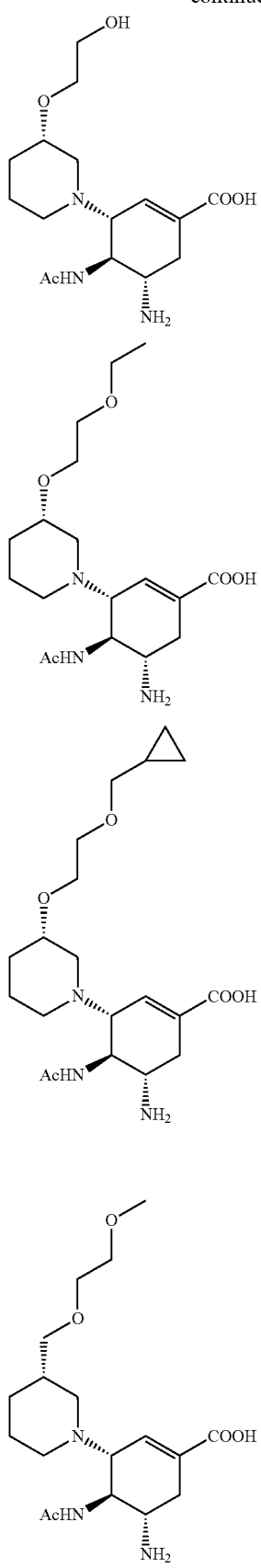
60
-continued
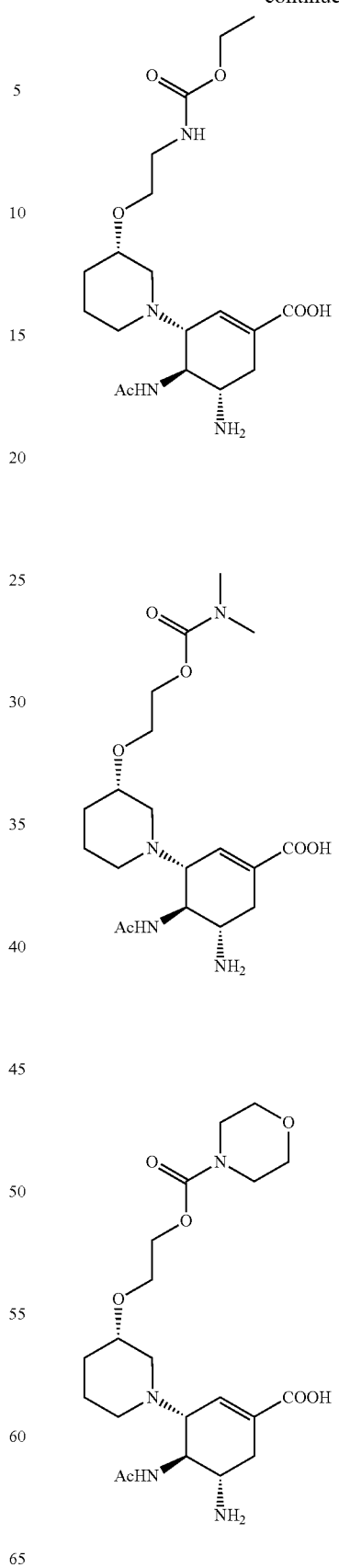

-continued

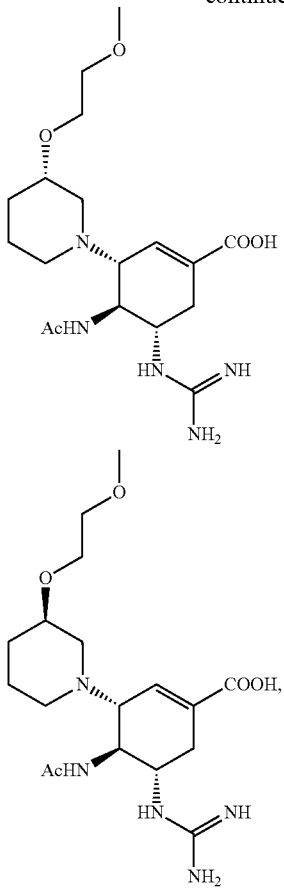

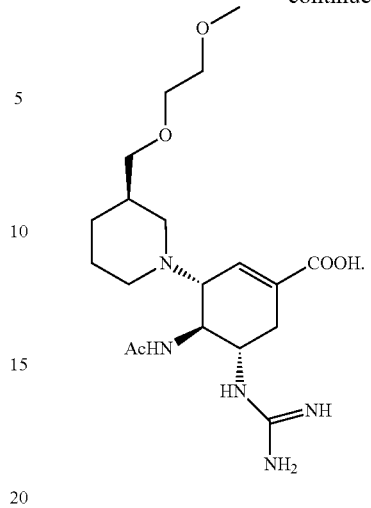

5. A pharmaceutical composition, comprising the cyclohexene compound or a pharmaceutically acceptable salt, or a stereoisomer thereof according to claim 1, and a pharmaceutically acceptable excipient or carrier.

6. The cyclohexene compound or a pharmaceutically acceptable salt, or a stereoisomer thereof according to claim 2, wherein,
the substituted $C_1$-$C_4$ alkyl is selected from hydroxyethyl, methoxyethyl, ethoxyethyl, or cyclopropylmethyl; and
the substituted $C_3$-$C_6$ heterocyclyl is selected from morpholine-4-carbonyloxy.

* * * * *